(12) United States Patent
Buyyarapu et al.

(10) Patent No.: US 9,840,744 B2
(45) Date of Patent: *Dec. 12, 2017

(54) MARKERS LINKED TO RENIFORM NEMATODE RESISTANCE

(71) Applicant: DOW AGROSCIENCES LLC, Indianapolis, IN (US)

(72) Inventors: Ramesh Buyyarapu, Zionsville, IN (US); Ruihua Ren, Carmel, IN (US); Mustafa McPherson, Leland, MS (US); Siva P. Kumpatla, Carmel, IN (US); Chandra Channabasavaradhya, Carmel, IN (US); Joseph W. Spinks, Indianapolis, IN (US); Kelly Parliament, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 488 days.

This patent is subject to a terminal disclaimer.

(21) Appl. No.: 14/210,895

(22) Filed: Mar. 14, 2014

(65) Prior Publication Data

US 2014/0283212 A1    Sep. 18, 2014

Related U.S. Application Data

(60) Provisional application No. 61/799,059, filed on Mar. 15, 2013.

(51) Int. Cl.
*C12Q 1/68* (2006.01)
*C12N 15/82* (2006.01)

(52) U.S. Cl.
CPC ....... *C12Q 1/6895* (2013.01); *C12N 15/8285* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 2011/0088118 | A1 | 4/2011 | Bhatti et al. |
| 2011/0173713 | A1* | 7/2011 | Bhatti ............... A01H 1/04 800/265 |

FOREIGN PATENT DOCUMENTS

| WO | 9932661 | 7/1999 |
| WO | 2008054546 | 5/2008 |
| WO | 2010025172 | 3/2010 |
| WO | 2011044550 | 4/2011 |
| WO | 2010038476 | 3/2012 |

OTHER PUBLICATIONS

Stephens and Finkner, 1953, Economic Botany 52: 257-269.*
Gutiérrez et al., 2011, Theor. Appl. Genetics 122: 271-280.*
Batley and Edwards, 2007, In: Association Mapping in Plants, pp. 95-102.*
Blenda et al., 2012, PLoS One 7(9): e45739, pp. 1-17.*
Starr et al., 2007, Journal of Nematology 39: 283-294.*
Starr, et al., "The future of nematode management in cotton," Journal of Nematology, 2007, pp. 283-294, vol. 39. No. 4.
Ulloa, "Mapping Fusarium wilt race 1 resistance genes 1n cotton by inheritance, QTL and sequencing composition," Molecular Genetics and Genomics, 2011, pp. 21-36, vol. 286, No. 1.
Agudelo, Paula et al., "Histological observations of rotylenchulus reniformis on Gossypium longicalyx and interspecific cotton hybrids," Journal of Nematology, 2005, pp. 444-447, vol. 37., No. 4.
Boyle, Patrick et al., "The BTB/POZ domain of the Arabidopsis disease resistance protein NPR1 interacts with the repression domain of TGA2 to negate is function," The Plant Cell, Nov. 2009, pp. 3700-3713, vol. 21.
Dighe, Nilesh D., "Linkage mapping of resistance to reniform nematode in cotton following introgression from Gossypium longicalyx," Crop Science, Jul.-Aug. 2009, pp. 1151-1164, vol. 49.
Gotz, Stefan, "High-throughput function annotation and date mining with the Blst2GO suite," Nucleic Acids Research, pp. 3420-3435, 2008, vol. 36, No. 10.
Gutierrez, et al., Identification of QLT regions and SSR markers associated with resistance to reniform nematode in Gossypium barbadense L. accession GB713, Theoretical and Applied Genetics, pp. 271-280 ,vol. 122, No. 2.
Gutierrez, et al., SSR markers closely associated with genes for resistance to root-knot nematode on chromosomes 11 and 14 of Upland cotton, Theoretical and Applied Genetics, pp. 1323-1337 ,vol. 121, No. 7.
Hendrix, Bill et al., "Estimation of nuclear DNA content of Gossypium species" Annals of Botany, 2005, pp. 789-797, vol. 95.
International Search Report and Written Opinion for PCT/US2014/027300, dated Jul. 1, 2014.
Kohel, Russel J., et al., "Molecular mapping and characterization of traits controlling fiber quality in cotton," Euphytica, 2001, pp. 163-172, vol. 121.
Lafoe, J., et al., "Resistance to renifomr nematode in exotic cotton lines," Natinal Cotton Council Beltwide Cotton Conference, Jun. 1, 2005, abstract only.
Miller, Robert NG., et al., "Analysis of non-TIR NBS-LRR resistance gene analogs in Musa acuminate colla: isolation, RFLP marker development, and physical mapping," BMC Plant Biology, 2008, 15 pages, vol. 8, No. 15.
Oeveren, Jan van, et al., "Mining SNPs form DNA sequence data," Computational approaches to SNP discovery and analysis 19 pages.
Ooijen, gerben van, et al., "structure-function analysis of the NB-ARC domain of plant disease resistance proteins," Journal of Experimental Botany, 2008, pp. 1383-1397, vol. 59, No. 6.

*Primary Examiner* — Amjad Abraham
*Assistant Examiner* — Bratislav Stankovic
(74) *Attorney, Agent, or Firm* — Marcia I. Rosenfeld; Magleby Cataxinos & Greenwood

(57) ABSTRACT

This disclosure concerns methods and compositions for identifying cotton plants that have a reniform nematode resistance trait. Some embodiments concern molecular markers to identify, select, and/or construct reniform nematode resistant plants and germplasm, or to identify and counter-select relatively susceptible plants. This disclosure also concerns cotton plants comprising a reniform nematode resistance trait that are generated by methods utilizing at least one marker described herein.

9 Claims, 6 Drawing Sheets

(56) References Cited

OTHER PUBLICATIONS

Reinisch, Alesia J., et al., "A detailed RFLP map of cotton, *Gossypium hirsutum* x *Gossypium babbadense*: chromosome organization and evolution in a disomic polyploidy genome," Genetics, Nov. 1994, pp. 829-847, vol. 13.
Robbins, R. T., et al., "Reproduction of the reniform nematode on thirty soybean cultivars," Supplement to Journal of Nematoloyg, 1994, pp. 659-664, vol. 26, No. 4S.
Robinson, A. Forest, "Reniform in US cotton: when, where, why and some remedies," Agrucultural Research Service, US Department of Agriculture, Annu. Rev. Phytopathol, 2007, pp. 263-288, vol. 45.
Romana, Gabrielea Beatriz, et al., "Identification and genomic location of a reniform nematode (*Rotylenchulus reniformis*) resistance locus (Renari)introgressed from Gossypium ariduminto upland cotton (*G. hirsutum*)," Theor Appl Genet, 2009, pp. 139-150, vol. 120.
Vos, Pieter et al., "The tomato mi-1 gene confers resistance to both root-knot nematodes and potato aphids," Nature Biotechnolyg, Dec. 1998, pp. 1365-1369, vol. 16.
Weaver, David B., et al., "Reniform nematode resistance in upland cotton germplasm," Crop Science, Jan. 2007, pp. 19-24, vol. 47.
Hinchliffe, et al., "Resistance gene analogue markers are mapped to homeologous chromosomes in cultivated tetraploid cotton," Theoretical and Applied Genetics, 2005, pp. 1074-1085, vol. 110, No. 6.
Li et al. 2015; Nature Biotechnoology 33: 524-530.
Australian Government 2008, The Biology of *Gussypium hirsutum* L. and *Gussypium barbadense* L. (cotton) pp. 1-87, p. 51 only.

\* cited by examiner

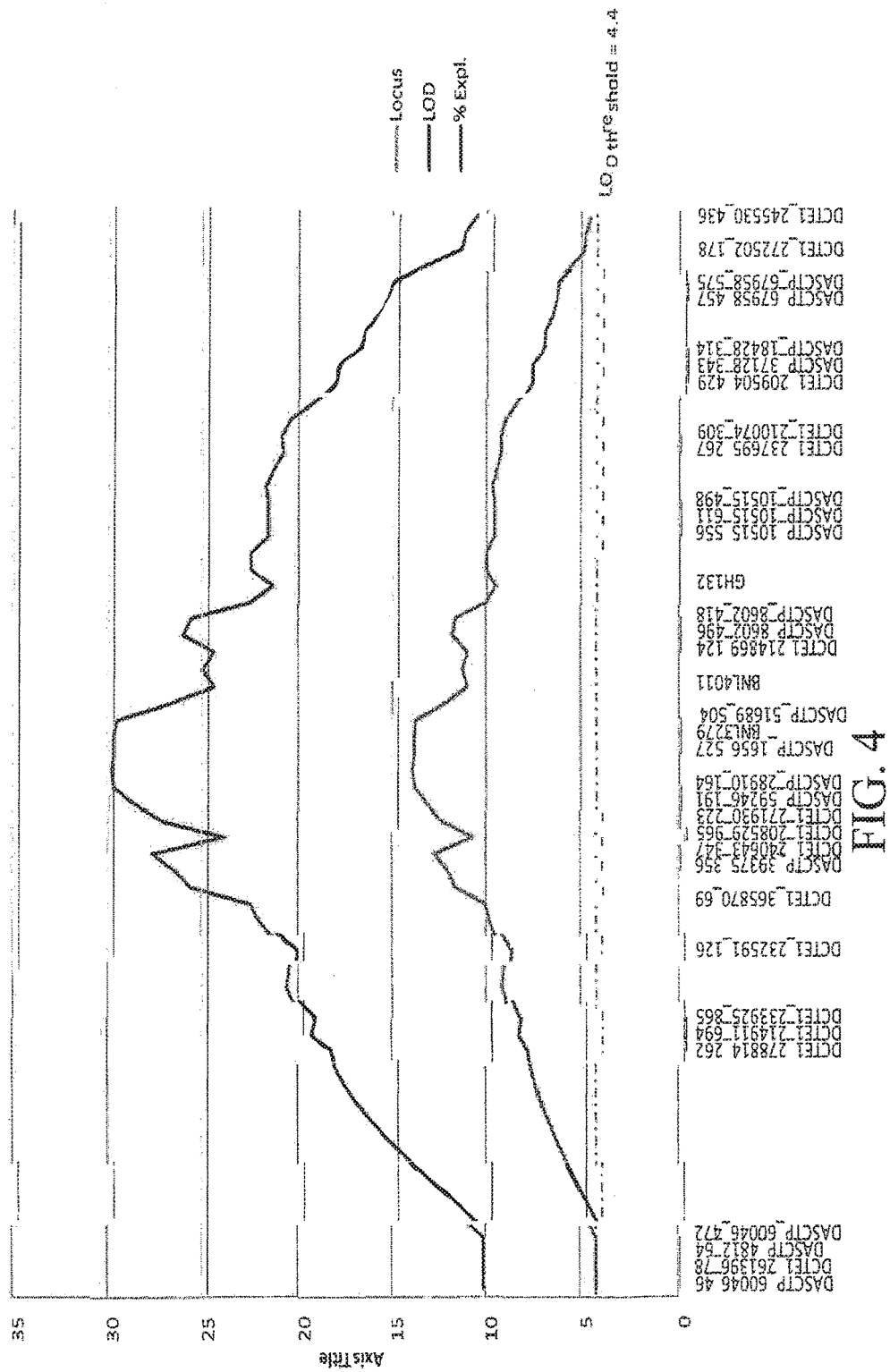

MARKERS LINKED TO RENIFORM NEMATODE RESISTANCE

CROSS-REFERENCE TO RELATED APPLICATION

This application claims the benefit of U.S. Provisional Patent Application Ser. No. 61/799,059, filed Mar. 15, 2013, the disclosure of which is hereby incorporated herein in its entirety by this reference.

TECHNICAL FIELD

The present disclosure relates to plant disease resistance. In some embodiments, the disclosure relates to reniform nematode resistance, for example, in cotton. In particular embodiments, the disclosure relates to compositions and methods for identifying a reniform nematode resistance trait in an organism, for example, molecular markers that are tightly linked to reniform nematode resistance. Further embodiments relate to compositions and methods for introducing a reniform nematode resistance trait into a host organism, for example, by using molecular markers tightly linked to reniform nematode resistance.

BACKGROUND

Cotton (*Gossypium* spp.) is an important fiber and oil seed crop throughout the world. In most other cotton-producing countries, including the United States, cotton is grown as an annual crop, although its natural growth habit is perennial in nature. The genus *Gossypium* comprises approximately 50 known species, which are native to and and semi-arid regions of the Americas, Asia, Africa and Australia. Fryxell (1992) *Rheedea* 2:108-65. These species populate several genomic groups based on chromosome size and homologous chromosome pairing in inter-specific hybrids, including eight groups of diploid plants and 1 group of tetraploid plants (i.e., "AD" genome). The majority of cotton fiber is produced by *G. hirsutum* ("Upland cotton"), which is a species of the tetraploid AD genome group. Furthermore, while cotton cultivation is largely dependent on these high-yielding Upland cotton cultivars, they are low in genetic variation relative to other plant taxa, and are considered to be vulnerable to pathogen and insect infection. Brubaker & Wendel (1994) *Am. J. Bot.* 81:1309-26; Bowman et al. (1996) *Crop Sci.* 36:577-81.

In recent years, the yields of cotton in many parts of USA and other nations has been affected by infection with the parasite, reniform nematode ("RN") (*Rotylenchulus reniformis*). Reniform nematode parasitism in cotton involves the formation of syncytia to provide nutrition for the developing female, and the events that occur at this feeding site may determine the degree of susceptibility of cotton plants to the nematode. Agudelo et al. (2005) *J. Nematology* 37:185-9; Rebois et al. (1975) *J. Nematology* 7:122-39.

There are few tools available to combat RN crop damage. For example, nematicides such as TEMIK® and soil fumigants such as TELON$^E$® have been used to reduce the detrimental effect of reniform nematodes on the yield of cotton, but these nematicides are only partially effective when they are used as indicated. Host plant resistance would be the most economically feasible means to manage reniform nematode infestations, but no Upland cotton cultivar is resistant to RN. Robinson et al. (1999) *Crop Sci.* 39:850-8; Koenning et al. (2004) *Plant Dis.* 88:100-13; Usery et al. (2005) *Nematropica* 35:121-33; Weaver et al. (2007) *Crop Sci.* 47:19-24.

Reniform nematode resistance has been identified in wild diploid species, such as *G. longicalyx* (Dighe et al. (2009) *Crop Sci.* 49:1151-64) and *G. aridium* (Romano et al. (2009), supra) as well as an allotetraploid genotype: Inca Cotton GB713 (Gutiérrez et al. (2011) TAG *Theor. Appl. Genet.* 122:271-80). A single dominant gene has been identified as responsible for the inheritance of RN resistance obtained from the introgression of *G. longicalyx* into *G. hirsutum*. Robinson et al. (2007) *Crop Sci.* 47:1865-77. In addition, dominant genes at two different loci have been identified as responsible for the inheritance of resistance to RN obtained from the introgression of *G. arboreum* and *G. aridum* (Rose & Standley) Skovsted. Sacks & Robinson (2009) *Field Crops Res.* 112:1-6. It is important to identify as many useful sources of RN resistance as possible. Multiple resistance sources may prove an invaluable resource if and when resistance-breaking nematode populations or races are encountered or develop.

The introgression of traits (e.g., RN resistance) from other sources into Upland cotton is a lengthy and challenging process, because for example, cotton genetics is complicated, involving differences in ploidy and the existence of various genomes and sub-genomes, many of which are incompatible or have low compatibility. Robinson (2007), *Annu. Rev. Phytopathol.* 45:263-88; Percival et al. (1999), "Taxonomy and germplasm resources," In *Cotton: Origin, History, Technology, and Production.* Smith & Cothren (eds.), New York, N.Y., John Wiley & Sons, pp. 33-63. Moreover, the survival of plants resulting from inter-specific crosses is low due to chromosome pairing difficulties, and there is an even lower probability of obtaining agronomically suitable progeny with the desired introgressed genetic material. See Romano et al. (2009) TAG *Theor. Appl. Genet.* 120:139-50. Where it has been possible, traits of interest have been introgressed into Upland cotton from diploid species via hexaploid bridging lines. See, e.g., Robinson et al. (2007), supra; Konan et al. (2007) *Plt. Breed* 126:176-81.

Plant breeding programs combine desirable traits from two or more cultivars or various broad-based sources into breeding pools, from which cultivars are developed by selfing and selection of desired phenotypes. The goal is to combine in a single variety an improved combination of desirable traits from the parental germplasm. There are numerous steps in such a program for the development of a new cultivar comprising one or more desired trait(s). Plant breeding begins with the analysis and definition of problems and weaknesses of the current germplasm, the establishment of program goals, and the definition of specific breeding objectives. Germplasm that possess the traits to meet the program goals must be selected, where any two germplasms may be incompatible or poorly compatible, particularly in the case of a plant such as cotton, which has complicated genetics.

Each breeding program should include a periodic, objective evaluation of the efficiency of the breeding procedure. Evaluation criteria vary depending on the goal and objectives, but should include gain from selection per year (based on comparisons to an appropriate standard), overall value of the advanced breeding lines, and the number of successful cultivars produced per unit of input (e.g., per year, per dollar expended, etc.). Promising advanced breeding lines are then thoroughly tested and compared to appropriate standards in environments representative of the commercial target area(s) for three or more years. Candidates for new commercial cultivars are selected from among the best lines; those still deficient in a few traits may be used as parents to produce new populations for further selection. These processes, which lead to the final step of marketing and distribution, usually take from 8 to 12 years from the time the first cross is made. Therefore, development of new cultivars is a time-consuming process that requires precise forward planning, efficient use of resources, and a minimum of changes in direction.

A most difficult task in plant breeding is the identification of individuals that are genetically superior. One method of identifying a superior plant is to observe its performance relative to other experimental plants and to a widely grown standard cultivar. If a single observation is inconclusive, replicated observations may be used to provide a better estimate of its genetic worth. This task is extremely difficult, because (for most traits) the true genotypic value is masked by other confounding plant traits or environmental factors.

The practitioner's choice of breeding and selection methods depends on the mode of plant reproduction, the heritability of the trait(s) being improved, the type of cultivar used commercially (e.g., $F_1$ hybrid cultivar, pureline cultivar, etc.), and the complexity of the trait's inheritance. For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection. Backcross breeding may be used to transfer one or a few favorable genes for a highly heritable trait into a desirable cultivar. Various recurrent selection techniques may be used to improve quantitatively-inherited traits controlled by numerous genes.

The breeder initially selects and crosses two or more parental lines, followed by repeated selfing and selection, producing many new genetic combinations. The breeder can theoretically generate billions of different genetic combinations via crossing, selfing, and mutagenesis. Such a breeder has no direct control of the process at the cellular level. Therefore, two breeders will never develop the same line, or even very similar lines, having the same traits.

Each year, the plant breeder selects the germplasm to advance to the next generation. This germplasm is grown under unique and different geographical, climatic, and soil conditions. Further selections are then made, during and at the end of the growing season. The cultivars that are developed are unpredictable. This unpredictability is due to the breeder's selection, which occurs in unique environments, and which allows no control at the DNA level (using conventional breeding procedures), with millions of different possible genetic combinations being generated. A breeder of ordinary skill in the art cannot predict the final resulting lines he develops, except possibly in a very gross and general fashion. Similarly, the same breeder cannot produce the same cultivar twice by using the exact same original parents and the same selection techniques. In the process of developing superior new cotton cultivars, this unpredictability results in the expenditure of large amounts of resources, monetary and otherwise.

Marker-assisted selection (MAS) may be used when it is available to provide significant advantages with respect to time, cost, and labor, when compared to phenotyping in the selection of progeny plants. Single nucleotide polymorphism (SNP) markers have become the markers of choice for MAS in several crop improvement programs, because of their higher abundance, amenability for automation, and availability of high throughput genotyping platforms. However, in cultivated cotton species, the high genomic complexity, narrow genetic base, allotetraploid nature, and lack of a reference genome hinder the development of candidate SNP markers.

DISCLOSURE

Molecular markers that are linked to reniform nematode resistance may be used to facilitate marker-assisted selection for the reniform nematode resistance trait in cotton. Disclosed herein are particular markers identified to be within or near reniform nematode resistance QTL regions in a cotton genome that are polymorphic between a parent Upland cotton genotype and a RN resistance source, wherein the markers are linked (e.g., tightly-linked) to a reniform nematode resistance phenotype. In embodiments, a molecular marker linked to reniform nematode resistance may be selected from the group consisting of the markers set forth in Tables 2-4; and markers linked to any of the markers set forth in Tables 2-4. For example, a molecular marker linked to reniform nematode resistance may be selected from the group consisting of the markers set forth in Tables 3-4, and markers linked to any of the markers set forth in Tables 3-4. Such markers may offer superior utility in marker-assisted selection of cotton plants and cultivars that are resistant to damage from reniform nematode infestation.

Described herein are methods of identifying a first cotton plant that comprises reniform nematode resistance or germplasm comprised within such a cotton plant. For example, particular markers may be utilized to identify a reniform resistant *G. hirsutum* plant or germplasm comprising a reniform resistance QTL derived from an Inca Cotton GB713 parent. A first cotton plant or germplasm that comprises reniform nematode resistance may in some examples be a plant or germplasm that has a lower (i.e., reduced) susceptibility to reniform nematode infection and/or damage than is observed in a parental plant or germplasm of the first plant or germplasm. A first cotton plant or germplasm that comprises reniform nematode resistance may in some examples be a plant or germplasm that has a lower (i.e., reduced) susceptibility to reniform nematode infection and/or damage than is observed in a particular conventional plant or germplasm of the same species (e.g., *G. hirsutum*) as the first plant or germplasm. Some embodiments of such methods may comprise detecting in the first cotton plant or germplasm at least one marker linked to reniform nematode resistance.

Also described are methods of producing a cotton plant or germplasm comprising reniform nematode resistance. Some embodiments of such methods may comprise introgressing at least one marker linked to reniform nematode resistance from a first cotton plant or germplasm (e.g., a *G. barbadense* plant or germplasm) into a second cotton plant or germplasm (e.g., a *G. hirsutum* plant or germplasm) to produce a cotton plant or germplasm that is likely to comprise reniform nematode resistance. A cotton plant or germplasm produced by the foregoing methods is also included in particular embodiments.

Some embodiments include methods for producing a transgenic cotton plant. Examples of such methods may comprise introducing one or more exogenous nucleic acid molecule(s) into a target cotton plant or progeny thereof, wherein at least one of the exogenous nucleic acid molecule(s) comprises a cotton genomic nucleotide sequence that is linked to at least one marker linked to reniform nematode resistance, or wherein at least one of the exogenous nucleic acid molecule(s) comprises a nucleotide sequence that is specifically hybridizable to a nucleotide sequence that is linked to at least one marker linked to reniform nematode resistance.

Some embodiments include systems and kits for identifying a cotton plant that is likely to comprise reniform nematode resistance. Particular examples of such systems and kits may comprise a set of nucleic acid probes, each comprising a nucleotide sequence that is specifically hybridizable to a nucleotide sequence that is linked in cotton to at least one marker that is linked to reniform nematode resistance. Particular examples of systems and kits for identifying a cotton plant that is likely to comprise reniform nematode resistance may comprise a detector that is configured to detect one or more signal outputs from the set of nucleic acid probes, or an amplicon thereof, thereby identifying the presence or absence of the at least one marker that is linked to reniform nematode resistance. Specific examples include instructions that correlate the presence or absence of the at least one marker with the likely reniform nematode resistance.

The foregoing and other features will become more apparent from the following detailed description of several embodiments, which proceeds with reference to the accompanying figures.

SEQUENCE LISTING

Figure 1:
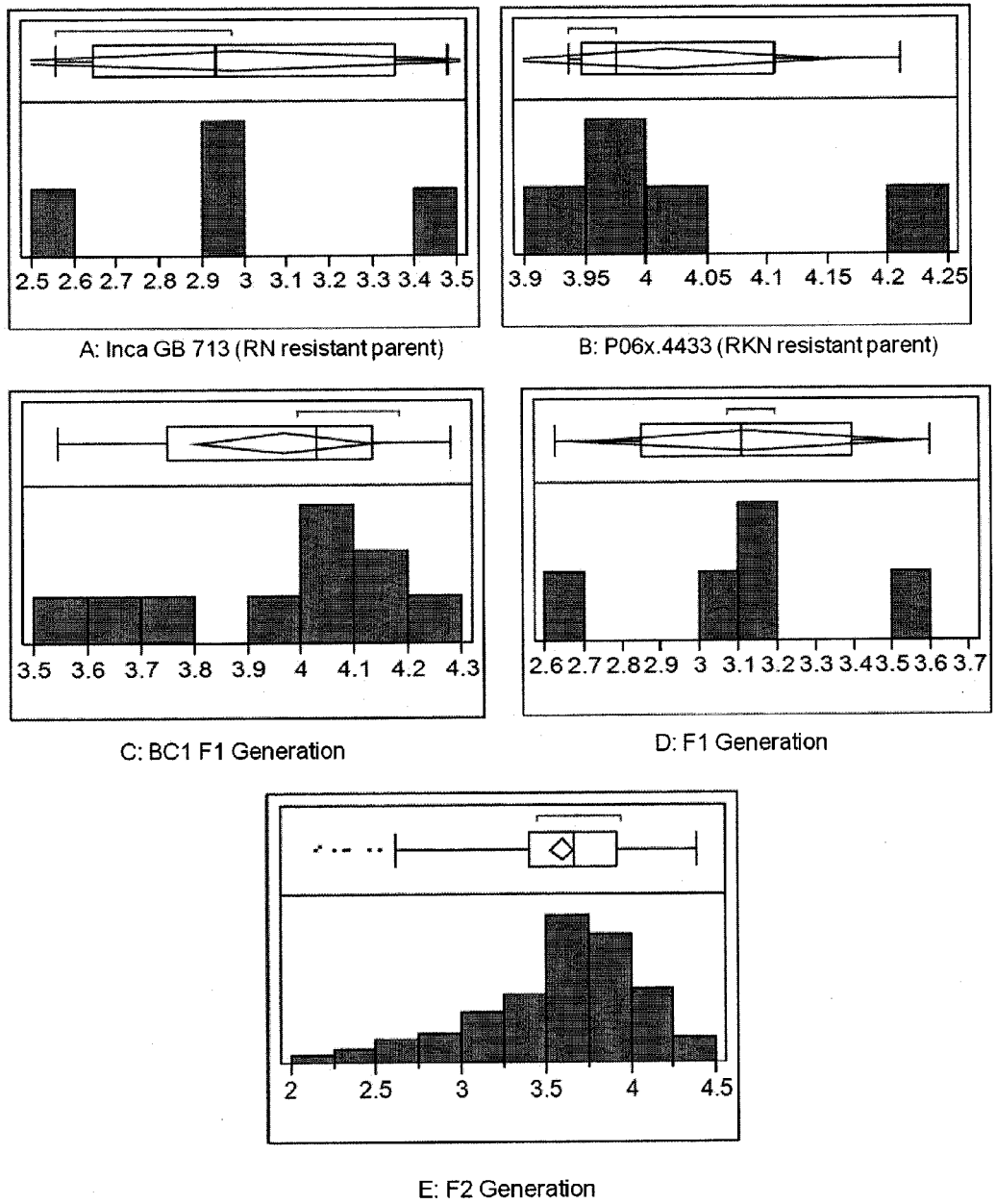
FIG. 1 includes frequency distributions of $\log_{10}(X+1)$ ratio for all samples in the study (a-e).

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NOs:1-21 show SNP markers linked to a major reniform resistance QTL on cotton chromosome 21.

SEQ ID NOs:22-27 show SSR markers linked to the QTLs on cotton chromosomes 21.

DETAILED DESCRIPTION

I. Overview of Several Embodiments

Embodiments of the invention involve particular molecular markers that are tightly linked to a reniform nematode resistance trait in the tetraploid *Gossypium barbadense* genotype, Inca Cotton GB 713. In some embodiments, these markers and their equivalents may be used to introgress a reniform nematode resistance trait from this source into agronomically desirable cotton species and cultivars (for example, to overcome the lack of host resistance to reniform nematode in cultivated cotton), or to identify the trait in a cotton plant or germplasm. It is desirable for a number of reasons to produce a cotton (e.g., *G. hirsutum*) having increased resistance to reniform nematode infection and/or damage, when compared to a conventional variety. It is further desirable to identify as many sources for reniform nematode resistance as possible, for example, to provide protection against resistance-breaking nematode populations or races, and/or to combine nematode resistance QTLs in a single germplasm to provide improved resistance. Embodiments herein provide high-throughput and cost-effective strategies and processes for the design and execution of RN resistance introgression programs.

Some embodiments include, for example, compositions and methods for identifying cotton plants comprising a reniform nematode resistance trait from the tetraploid *Gossypium barbadense* genotype, Inca Cotton GB 713, and/or germplasm carrying a genotype that is predictive and determinative of such a reniform nematode resistance trait. Methods of making such cotton plants and germplasm are included in some embodiments. Such methods may include, for example and without limitation, introgression of desired reniform nematode resistance marker alleles and/or genetic transformation methods. Cotton plants and/or germplasm made by methods such as the foregoing are included in particular embodiments. Systems and kits for selecting cotton plants comprising a reniform nematode resistance trait and/or germplasm carrying a genotype that is predictive and determinative of a reniform nematode resistance trait are also a feature of certain embodiments.

A process comprising identification and selection of cotton plants comprising a reniform nematode resistance trait using MAS is capable of providing an effective and environmentally friendly approach for generating pest-resistant agronomically-desirable cotton plants. Embodiments of the present invention provide a number of cotton marker loci and QTL chromosome intervals that demonstrate statistically significant co-segregation with (and therefore are predictive and determinative of) reniform nematode resistance. Detection of these markers, or additional loci linked to the markers that are therefore equivalent thereto, may be used in marker-assisted cotton breeding programs to produce reniform nematode resistant plants and germplasm.

Some embodiments provide methods for identifying a first cotton plant or germplasm (e.g., a line or variety) that displays reniform nematode resistance. In some examples, at least one allele of one or more marker locus (e.g., a plurality of marker loci) that is linked (e.g., tightly-linked) with a reniform nematode resistance trait from the tetraploid *Gossypium barbadense* genotype, Inca Cotton GB 713, is/are detected in the first cotton plant or germplasm. In examples, the marker loci may be selected from the loci in Tables 2-4 and markers linked to any of the markers set forth in Tables 2-4, including: DASCTP_4812_64; DASCTP_60046_472; DCTE1_261396_78; DASCTP_60046_46; DCTE1_278814_262; DCTE1_214911_694; DCTE1_233925_865; DCTE1_232591_126; DCTE1_365870_69; DASCTP_39375_356; DCTE1_240643_347; DCTE1_208529_965; DCTE1_271930_223; DASCTP_59246_191; DASCTP_28910_164; DASCTP_1656527; DASCTP_51689_504; DCTE1_214869_124; DASCTP_8602_496; DASCTP_8602_418; DASCTP_10515_556; BNL3279; BNL4011; GH132; and other markers that are linked to at least one of the foregoing QTL markers.

In some examples, a plurality of maker loci may be selected or identified in the same plant or germplasm. All combinations of, for example, the marker loci set forth in Tables 2-4; and marker loci linked to any of the marker loci set forth in Tables 2-4, may be included in a plurality of marker loci to be selected or identified in a plant or germplasm. In some examples, the efficiency of marker detection from homeologous cotton genomes may be increased by a process (referred to herein as a "HAPSNP pipeline") comprising generating sequence contigs at high-stringency using sequence assembly programs, initial detection of putative SNPs, generating haplotype information and allelic frequency of loci in respective genotypes; enhancing the ability to identify high quality SNPs using allelic and haplotype frequency to discriminate paralogouslhomoeologous SNPs from homologous SNPs. This may be done in accordance with the method disclosed in International Patent Application No. PCT/US13/020211, the entire disclosure of which is incorporated by reference into the present application.

In some embodiments, a reniform nematode resistant cotton plant comprises a heterologous nucleic acid (e.g., at least one gene) from the RN resistance QTL of *G. barbadense* Inca Cotton GB 713 capable of conferring or improving RN resistance to a cotton plant or germplasm comprising the heterologous nucleic acid. Molecular markers according to particular examples may be utilized to identify and sequence such a nucleic acid.

II. Abbreviations

AFLP amplified fragment length polymorphism
ASH allele specific hybridization
cM centiMorgans
EST expressed sequence tag
LG linkage group
LOD logarithm (base 10) of odds
MAS marker-assisted selection
NASBA nucleic acid sequence based amplification
PCR polymerase chain reaction
QTL quantitative trait locus
RAPD randomly amplified polymorphic DNA
RFLP restriction fragment length polymorphism
RIL recombinant inbred line
RKN root knot nematode
RN reniform nematode
RT-PCR reverse transcriptase-PCR
SNP single nucleotide polymorphism
SSCP single-strand conformation polymorphism
SSR simple sequence repeat

III. Terms

As used in this application, including the claims, terms in the singular and the singular forms (for example, "a," "an," and "the") include plural referents, unless the content clearly indicates otherwise. Thus, for example, a reference to "plant," "the plant," or "a plant" also refers to a plurality of plants. Similarly, a reference to "marker," "the marker," or "a marker" also refers to a plurality of markers. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules, and the term, "marker," may refer to many similar or identical markers.

Numeric ranges are inclusive of the numbers defining the range, and include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component. For example and without limitation, a nucleic acid may be isolated from a chromosome by breaking chemical bonds connecting the nucleic acid to the remaining DNA in the chromosome. Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides, linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Mapping population: As used herein, the term "mapping population" may refer to a plant population (e.g., a cotton plant population) used for genetic mapping. Mapping populations are typically obtained from controlled crosses of parent genotypes, as may be provided by two inbred lines. Decisions on the selection of parents, mating design for the development of a mapping population, and the type of markers used depend upon the gene to be mapped, the availability of markers, and the molecular map. The parents of plants within a mapping population should have sufficient variation for a trait(s) of interest at both the nucleic acid sequence and phenotype level. Variation of the parents' nucleic acid sequence is used to trace recombination events in the plants of the mapping population.

The availability of informative polymorphic markers is dependent upon the amount of nucleic acid sequence variation. Thus, a particular informative marker may not be identified in a particular cross of parent genotypes, though such markers may exist.

A "genetic map" is a description of genetic linkage relationships among loci on one or more chromosomes (or linkage groups) within a given species, as may be determined by analysis of a mapping population. In some examples, a genetic map may be depicted in a diagrammatic or tabular form. The term "genetic mapping" may refer to the process of defining the linkage relationships of loci through the use of genetic markers, mapping populations segregating for the markers, and standard genetic principles of recombination frequency. A "genetic map location" refers to a location on a genetic map (relative to surrounding genetic markers on the same linkage group or chromosome) where a particular marker can be found within a given species. In contrast, a "physical map of the genome" refers to absolute distances (for example, measured in base pairs or isolated and overlapping contiguous genetic fragments) between markers within a given species. A physical map of the genome does not necessarily reflect the actual recombination frequencies observed in a test cross of a species between different points on the physical map.

Cross: As used herein, the term "cross" (or "crossed") refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into plants. The backcrossing technique has been widely used for decades to introduce new traits into plants. N. Jensen, Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Introgression: As used herein, the term "introgression" refers to the transmission of an allele at a genetic locus into a genetic background. In some embodiments, introgression of a specific allele form at the locus may occur by transmitting the allele form to at least one progeny via a sexual cross between two parents of the same species, where at least one of the parents has the specific allele form in its genome. Progeny comprising the specific allele form may be repeatedly backcrossed to a line having a desired genetic background. Backcross progeny may be selected for the specific allele form, so as to produce a new variety wherein the specific allele form has been fixed in the genetic background. In some embodiments, introgression of a specific allele form may occur by recombination between two donor genomes (e.g., in a fused protoplast), where at least one of the donor genomes has the specific allele form in its genome. Introgression may involve transmission of a specific allele form that may be, for example and without limitation, a selected allele form of a marker allele; a QTL; and/or a transgene.

Germplasm: As used herein, the term "germplasm" refers to genetic material of or from an individual plant or group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells).

As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a cotton line or variety. In particular examples, a germplasm is seed of the cotton line or variety. In particular examples, a germplasm is a nucleic acid sample from the cotton line or variety.

Gene: As used herein, the term "gene" (or "genetic element") may refer to a heritable genomic DNA sequence with functional significance. The term "gene" may also be used to refer to, for example and without limitation, a cDNA and/or an mRNA encoded by a heritable genomic DNA sequence.

Genotype: As used herein, the term "genotype" refers to the genetic constitution of an individual (or group of individuals) at one or more particular loci. The genotype of an individual or group of individuals is defined and described by the allele forms at the one or more loci that the individual has inherited from its parents. The term genotype may also be used to refer to an individual's genetic constitution at a single locus, at multiple loci, or at all the loci in its genome. A "haplotype" is the genotype of an individual at a plurality of genetic loci. In some examples, the genetic loci described by a haplotype may be physically and genetically linked; i.e., the loci may be positioned on the same chromosome segment.

Elite: As used herein, the term "elite" refers to a variety or cultivar that has been bred and selected for superior agronomic performance. Elite cotton lines include, for example and without limitation, DP 555 BG/RR, DP 445 BG/RR, DP 444 BG/RR, DP 454 BG/RR, DP 161 B2RF, DP 141 B2RF, DP 0924 B2RF, DP 0935 B2RF, DP 121 RF, and DP 174 RF (Deltapine); ST5599BR, ST5242BR, ST4554B2RF, ST4498B2RF, and ST5458B2RF (Stoneville); FM9058F, FM9180B2F, FM1880B2F, and FM1740B2F (Fiber-Max); PHY485WRF, PHY375WRF, and PHY745WRF (PhytoGen); and MCS0423B2RF, and MCS0508B2RF (Cotton States).

Quantitative trait locus: Specific chromosomal loci (or intervals) may be mapped in an organism's genome that correlate with particular quantitative phenotypes. Such loci are each termed a "quantitative trait locus," or QTL. As used herein, the term "quantitative trait locus" refers to stretches of DNA that have been identified as likely DNA sequences (e.g., genes, non-coding sequences, and/or intergenic sequences) that underlie a quantitative trait, or phenotype, that varies in degree, and can be attributed to the interactions between two or more DNA sequences (e.g., genes, non-coding sequences, and/or intergenic sequences) or their expression products and their environment. Thus, the term "quantitative trait locus" includes polymorphic genetic loci with at least two alleles that differentially affect the expression of a phenotypic trait in at least one genetic background (e.g., in at least one breeding population or progeny). In practice, QTLs can be molecularly identified to help map regions of the genome that contain sequences involved in specifying a quantitative trait, such as RN resistance.

As used herein, the term "QTL interval" may refer to stretches of DNA that are linked to the gene(s) that underlie the QTL trait. A QTL interval is typically, but not necessarily, larger than the QTL itself. A QTL interval may contain stretches of DNA that are 5' and/or 3' with respect to the QTL.

Multiple experimental paradigms have been developed to identify and analyze QTLs. See, e.g., Jansen (1996) *Trends Plant Sci.* 1:89. The majority of published reports on QTL mapping in crop species have been based on the use of a bi-parental cross. See Lynch and Walsh (1997) *Genetics and Analysis of Quantitative Traits*, Sinauer Associates, Sunderland. Typically, these paradigms involve crossing one or more parental pairs that can be, for example, a single pair derived from two inbred strains, or multiple related or unrelated parents of different inbred strains or lines, which each exhibit different characteristics relative to the phenotypic trait of interest. Typically, this experimental protocol involves deriving 100 to 300 segregating progeny from a single cross of two divergent inbred lines that are, for example, selected to maximize phenotypic and molecular marker differences between the lines. The parents and segregating progeny are genotyped for multiple marker loci, and evaluated for one to several quantitative traits (e.g., RN resistance). QTLs are then identified as significant statistical associations between genotypic values and phenotypic variability among the segregating progeny.

The strength or weakness of this experimental protocol is determined by the utilization of the inbred cross, because the resulting $F_1$ parents all have the same linkage phase (how the alleles were joined in the parental generation). Thus, after selfing of $F_1$ plants, all segregating $F_2$ progeny are informative and linkage disequilibrium is maximized, the linkage phase is known, there are only two QTL alleles, and (except for backcross progeny) the frequency of each QTL allele is 0.5.

Numerous statistical methods for determining whether markers are genetically linked to a QTL (or to another marker) are known to those of skill in the art and include, for example and without limitation, standard linear models (e.g., ANOVA or regression mapping; Haley and Knott (1992) *Heredity* 69:315); and maximum likelihood methods (e.g., expectation-maximization algorithms; Lander and Botstein (1989) *Genetics* 121:185-99; Jansen (1992) *Theor. Appl. Genet.* 85:252-60; Jansen (1993) *Biometrics* 49:227-31; Jansen (1994) "Mapping of quantitative trait loci by using genetic markers: an overview of biometrical models," In J. W. van Ooijen and J. Jansen (eds.), *Biometrics in Plant breeding: applications of molecular markers*, pp. 116-24, CPRO-DLO Metherlands; Jansen (1996) *Genetics* 142:305-11; and Jansen and Stam (1994) *Genetics* 136:1447-55).

Exemplary statistical methods include single point marker analysis; interval mapping (Lander and Botstein (1989) *Genetics* 121:185); composite interval mapping; penalized regression analysis; complex pedigree analysis; MCMC analysis; MQM analysis (Jansen (1994) *Genetics* 138:871); HAPLO-IM+ analysis, HAPLO-MQM analysis, and HAPLO-MQM+ analysis; Bayesian MCMC; ridge regression; identity-by-descent analysis; and Haseman-Elston regression, any of which are suitable in the context of particular embodiments of the invention. Alternative statistical methods applicable to complex breeding populations that may be used to identify and localize QTLs in particular examples are described in U.S. Pat. No. 6,399,855 and PCT International Patent Publication No. WO0149104 A2. All of these approaches are computationally intensive and are usually performed with the assistance of a computer-based system comprising specialized software. Appropriate statistical packages are available from a variety of public and commercial sources, and are known to those of skill in the art.

Marker: Although specific DNA sequences that encode proteins are generally well-conserved across a species, other regions of DNA (e.g., non-coding DNA and introns) tend to develop and accumulate polymorphism, and therefore may be variable between individuals of the same species. The genomic variability can be of any origin, for example, the variability may be due to DNA insertions, deletions, duplications, repetitive DNA elements, point mutations, recombination events, and the presence and sequence of transposable elements. Such regions may contain useful molecular genetic markers. In general, any differentially inherited polymorphic trait (including nucleic acid polymorphisms) that segregates among progeny is a potential marker.

As used herein, the terms "marker" and "molecular marker" refer to a nucleic acid or encoded product thereof (e.g., a protein) used as a point of reference when identifying a linked locus. Thus, a marker may refer to a gene or nucleic acid that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" or "marker allele form" refers to the version of the marker that is present in a particular individual. The term "marker" as used herein may refer to a cloned segment of chromosomal DNA, and may also or alternatively refer to a DNA molecule that is complementary to a cloned segment of chromosomal DNA. The term also refers to nucleic acid sequences complementary to genomic marker sequences, such as nucleic acid primers and probes.

A marker may be described, for example, as a specific polymorphic genetic element at a specific location in the genetic map of an organism. A genetic map may be a graphical representation of a genome (or a portion of a genome, such as a single chromosome) where the distances between landmarks on the chromosome are measured by the recombination frequencies between the landmarks. A genetic landmark can be any of a variety of known polymorphic markers, for example and without limitation: simple sequence repeat (SSR) markers; restriction fragment length polymorphism (RFLP) markers; and single nucleotide polymorphism (SNP) markers. As one example, SSR markers can be derived from genomic or expressed nucleic acids (e.g., expressed sequence tags (ESTs)).

Additional markers include, for example and without limitation, ESTs; amplified fragment length polymorphisms (AFLPs) (Vos et al. (1995) *Nucl. Acids Res.* 23:4407; Becker et al. (1995) *Mol. Gen. Genet.* 249:65; Meksem et al. (1995) *Mol. Gen. Genet.* 249:74); randomly amplified polymorphic DNA (RAPD); and isozyme markers. Isozyme markers may be employed as genetic markers, for example, to track isozyme markers or other types of markers that are linked to a particular first marker. Isozymes are multiple forms of enzymes that differ from one another with respect to amino acid sequence (and therefore with respect to their encoding nucleic acid sequences). Some isozymes are multimeric enzymes containing slightly different subunits. Other isozymes are either multimeric or monomeric, but have been cleaved from a pro-enzyme at different sites in the pro-enzyme amino acid sequence. Isozymes may be characterized and analyzed at the protein level or at the nucleic acid level. Thus, any of the nucleic acid based methods described herein can be used to analyze isozyme markers in particular examples.

"Genetic markers" include alleles that are polymorphic in a population, where the alleles of may be detected and distinguished by one or more analytic methods (e.g., RFLP analysis, AFLP analysis, isozyme marker analysis, SNP analysis, and SSR analysis). The term "genetic marker" may also refer to a genetic locus (a "marker locus") that may be used as a point of reference when identifying a genetically linked locus (e.g., a QTL). Such a marker may also be referred to as a "QTL marker."

The nature of the foregoing physical landmarks (and the methods used to detect them) vary, but all of these markers are physically distinguishable from each other (as well as from the plurality of alleles of any one particular marker) on the basis of polynucleotide length and/or sequence. Numerous methods for detecting molecular markers and identifying marker alleles are well-established. A wide range of protocols are known to one of skill in the art for detecting this variability, and these protocols are frequently specific for the type of polymorphism they are designed to detect. Such protocols include, for example and without limitation, PCR amplification and detection of single-strand conformation polymorphism (SSCP), e.g., via electrophoresis; and self-sustained sequence replication (3SR) (See Chan and Fox (1999) *Reviews in Medical Microbiology* 10:185-96).

Molecular marker technologies generally increase the efficiency of plant breeding through MAS. A molecular marker allele that demonstrates linkage disequilibrium with a desired phenotypic trait (e.g., a QTL) provides a useful tool for the selection of the desired trait in a plant population. The key components to the implementation of an MAS approach are the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

Genetic variability, for example as determined in a mapping population, may be observed between different populations of the same species (e.g., cotton). In spite of the variability in the genetic map that may occur between populations of the same species, genetic map and polymorphic marker information derived from one population generally remains useful across multiple populations of different sub-species for the purposes of identification and/or selection of plants and/or germplasm comprising traits that are linked to the markers and counter-selection of plants and/or germplasm comprising undesirable traits.

Two types of markers used in particular MAS protocols described herein are SSR markers and SNP markers. SSR markers include any type of molecular heterogeneity that results in nucleic acid sequence length variability. Exemplary SSR markers are short (up to several hundred base pairs) segments of DNA that consist of multiple tandem repeats of a two or three base-pair sequence. These repeated sequences result in highly polymorphic DNA regions of variable length due to poor replication fidelity (e.g., by polymerase slippage). SSRs appear to be randomly dispersed through the genome, and are generally flanked by conserved regions. SSR markers may also be derived from RNA sequences (in the form of a cDNA, a partial cDNA, or an EST), as well as genomic material.

The heterogeneity of SSR markers make them well-suited for use as molecular genetic markers. For example, SSR genomic variability is inherited, and it is multi-allelic, co-dominant, and reproducibly detectable. The proliferation of increasingly sophisticated amplification-based detection techniques (e.g., PCR-based techniques) provides a variety of sensitive methods for the detection of nucleotide sequence heterogeneity between samples. Probes (e.g., nucleic acid primers) may be designed to hybridize to conserved regions that flank the SSR, and the probes may be used to amplify the variable SSR region. The differently sized amplicons generated from an SSR region have characteristic and reproducible sizes. Differently sized SSR amplicons observed from two homologous chromosomes from an individual, or from different individuals, in the plant population define SSR marker alleles. As long as there exist at least two SSR marker alleles that produce PCR products with different sizes, the SSR may be employed as a marker.

Linkage (dis)equilibrium: As used herein, the term "linkage equilibrium" refers to the situation where two markers independently segregate; i.e., the markers sort randomly among progeny. Markers that show linkage equilibrium are considered unlinked (whether or not they lie on the same chromosome). As used herein, the term "linkage disequilibrium" refers to the situation where two markers segregate in a non-random manner; i.e., the markers have a recombination frequency of less than 50% (and thus by definition, are separated by less than 50 cM on the same linkage group). In some examples, markers that show linkage disequilibrium are considered linked.

Linked, tightly linked, and extremely tightly linked: As used herein, linkage between genes or markers may refer to the phenomenon in which genes or markers on a chromosome show a measurable probability of being passed on together to individuals in the next generation. Thus, linkage of one marker to another marker or gene may be measured and/or expressed as a recombination frequency. The closer two genes or markers are to each other, the closer to "1" this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions).

In general, the closer one marker is to another marker or gene (whether the distance between them is measured in terms of genetic distance or physical distance), the more tightly they are linked. Because chromosomal distance is approximately proportional to the frequency of recombination events between traits, there is an approximate physical distance that correlates with recombination frequency.

As used herein, the term "linked" may refer to one or more genes or markers that are separated by a genetic distance of less than about 50 cM. Thus, two "linked" genes or markers may be separated by less than about 45 cM; less than about 40 cM; less than about 35 cM; less than about 30 cM; less than about 25 cM; less than about 20 cM; less than about 15 cM; less than about 10 cM; and less than about 5 cM.

As used herein, the term "tightly linked" may refer to one or more genes or markers that are located within about 35 cM of one another. Thus, two "tightly linked" genes or markers may be separated by less than 36 cM; less than 35 cM; less than 34 cM; less than about 33 cM; less than about 32 cM; less than about 31 cM; less than about 30 cM; less than about 29 cM; less than about 28 cM; less than about 27 cM; less than about 26 cM; less than about 25 cM; less than about 24 cM; less than about 23 cM; less than about 22 cM; less than about 21 cM; less than about 20 cM; less than about 19 cM; less than about 18 cM; less than about 17 cM; less than about 16 cM; less than about 15 cM; less than about 14 cM; less than about 13 cM; less than about 12 cM; less than about 11 cM; less than about 10 cM; less than about 9 cM; less than about 8 cM; less than about 7 cM; less than about 6 cM; less than about 5 cM; and even smaller genetic distances.

As used herein, the term "extremely tightly-linked" may refer to one or more genes or markers that are located within about 5.0 cM of one another. Thus, two "extremely tightly-linked" genes or markers may be separated by less than 6.0 cM; less than 5.5 cM; less than 5.0 cM; less than about 4.5 cM; less than about 4.0 cM; less than about 3.5 cM; less than about 3.0 cM; less than about 2.5 cM; less than about 2.0 cM; less than about 1.5 cM; less than about 1.0 cM; and less than about 0.5 cM.

The closer a particular marker is to a gene that encodes a polypeptide that contributes to a particular phenotype (whether measured in terms of genetic or physical distance), the more tightly-linked is the particular marker to the phenotype. In view of the foregoing, it will be appreciated that markers linked to a particular gene or phenotype include those markers that are tightly linked, and those markers that are extremely tightly linked, to the gene or phenotype. In some embodiments, the closer a particular marker is to a gene that contributes to RN resistance phenotype (whether measured in terms of genetic or physical distance), the more tightly-linked is the particular marker to the RN resistance phenotype. Thus, linked, tightly linked, and extremely tightly linked genetic markers of an RN resistance phenotype in cotton may be useful in MAS programs to identify cotton varieties comprising RN resistance (when compared to parental varieties and/or at least one particular conventional variety), to identify individual cotton plants comprising RN resistance, and to breed this trait into other cotton varieties (e.g., "AD" genome cotton, such as G. hirsutum) to increase resistance to RN infection and/or damage.

In some embodiments, the linkage relationship between a molecular marker and a phenotype may be expressed as a "probability" or "adjusted probability." Within this context, a probability value is the statistical likelihood that a particular combination of a phenotype and the presence or absence of a particular marker allele form is random. Thus, the lower the probability score, the greater the likelihood that the phenotype and the particular marker allele form will co-segregate. In some examples, the probability score may be described as "significant" or "non-significant." In particular examples, a probability score of 0.05 (p=0.05 (a 5% probability)) of random assortment is considered a "significant" indication of co-segregation. However, a significant probability may in other examples be any probability of less than 50% (p=0.5). For instance, a significant probability may be less than 0.25; less than 0.20; less than 0.15; and/or less than 0.1.

In some embodiments, a marker that is linked to an RN resistance phenotype may be selected from the cotton QTL markers of chromosomes 18 and 21 that are set forth in Tables 2-4. In some embodiments, a marker that is linked to an RN resistance phenotype may be selected from those markers that are located within about 10 cM of a QTL marker set forth in Tables 2-4. Thus, marker that is linked to an RN resistance phenotype may be, for example, within 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker set forth in Tables 2-4 (e.g., a QTL marker set forth in Tables 3-4). For example, a marker may be located between two QTL markers set forth in Tables 2-4.

A plant breeder can advantageously use molecular markers to identify desired individuals by identifying marker alleles that show a statistically significant probability of co-segregation with a desired phenotype (e.g., RN resistance), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select the phenotype by selecting for the proper molecular marker allele (i.e., MAS). The more molecular markers that are placed on the genetic map, the more potentially useful that map becomes for conducting MAS, and the more genetic backgrounds will be able to be utilized in the MAS process.

Marker set: As used herein, a "set" of markers or probes refers to a specific collection of markers or probes (or data derived therefrom) that may be used to identify individuals comprising a trait of interest. In some embodiments, a set of markers linked to an RN resistance phenotype may be used to identify a cotton plant comprising RN resistance. Data corresponding to a marker set or probe set (or data derived from the use of such markers or probes) may be stored in an electronic medium. While each marker in a marker set may possess utility with respect to trait identification, individual markers selected from the set and subsets including some, but not all, of the markers may also be effective in identifying individuals comprising the trait of interest.

Allele: As used herein, the term "allele" refers to one of two or more different nucleotide sequences that occur at a specific locus. For example, a first allele may occur on one chromosome, while a second allele may occur on a second homologous chromosome; e.g., as occurs for different chromosomes of a heterozygous individual, or between different homozygous or heterozygous individuals in a population. In some embodiments, a particular allele at a particular locus may be linked to an agronomically desirable phenotype (e.g., RN resistance). In some embodiments, a particular allele at the locus may allow the identification of plants that do not comprise the agronomically desirable phenotype (e.g., RN susceptible plants), such that those plants may be removed from a breeding program or planting. A marker allele may segregate with a favorable phenotype, therefore providing the benefit of identifying plants comprising the phenotype. An "allelic form of a chromosome segment" may refer to a chromosome segment that comprises a marker allele nucleotide sequence that contributes to, or is linked to, a particular phenotype at one or more genetic loci physically located on the chromosome segment.

"Allele frequency" may refer to the frequency (expressed as a proportion or percentage) at which an allele is present at a locus within a plant, within a line, or within a population of lines. Thus, for an allele "A," a diploid individual of genotype "AA," "Aa," "AB," or "aa," has an allele frequency of 1.0, 0.5, 0.5, or 0.0, respectively. The allele frequency within a line may be estimated by averaging the allele frequencies of a sample of individuals from that line. Similarly, the allele frequency within a population of lines may be calculated by averaging the allele frequencies of lines that make up the population. For a population with a finite number of individuals or lines, an allele frequency may be expressed as a count of individuals or lines (or any other specified grouping) containing the allele.

A marker allele "positively" correlates with a trait when the marker is linked to the trait, and when presence of the marker allele is an indicator that the desired trait or trait form will occur in a plant comprising the allele. A marker allele "negatively" correlates with a trait when the marker is linked to the trait, and when presence of the marker allele is an indicator that the desired trait or trait form will not occur in a plant comprising the allele.

A "homozygous" individual has only one form of allele at a given locus (e.g., a diploid plant having a copy of the same allele form at a particular locus for each of two homologous chromosomes). An individual is "heterozygous" if more than one allele form is present at the locus (e.g., a diploid individual having one copy of a first allele form and one copy of a second allele form at the locus). The term "homogeneity" refers to members of a group that have the same genotype (i.e., the same allele frequency) at one or more specific loci of interest. In contrast, the term "heterogeneity" refers to individuals within a group that differ in genotype at one or more specific loci of interest.

Any technique that may be used to characterize the nucleotide sequence at a locus may be used to identify a marker allele. Methods for marker allele detection include, for example and without limitation, molecular identification methods (e.g., amplification and detection of a marker amplicon). For example, an allelic form of an SSR marker, or of a SNP marker, may be detected by an amplification based technology. In a typical amplification-based detection method, a marker locus or a portion of the marker locus is amplified (using, e.g., PCR, LCR, and transcription using a nucleic acid isolated from a cotton plant of interest as an amplification template), and the resulting amplified marker amplicon is detected. In some embodiments, plant RNA may be utilized as the template for an amplification reaction. In some embodiments, plant genomic DNA may be utilized as the template for the amplification reaction. In some examples, the QTL marker is an SNP marker, and the detected allele is a SNP marker allele, and the method of detection is allele specific hybridization (ASH). In some examples, the QTL marker is an SSR marker, and the detected allele is an SSR marker allele.

ASH technology is based on the stable annealing of a short, single-stranded, oligonucleotide probe to a completely complementary single-strand target nucleic acid. Detection may be accomplished via detection of an isotopic or non-isotopic label attached to the probe. For each polymorphism, two or more different ASH probes may be designed to have identical DNA sequences, except at site of a polymorphism. Each probe may be perfectly homologous with one allele sequence, so that the range of probes can distinguish all the known alternative allele sequences. When each probe is hybridized to target DNA under appropriate probe design and hybridization conditions, a single-base mismatch between the probe and target DNA prevents hybridization. In this manner, only one of the alternative probes will hybridize to a target sample that is homozygous for an allele. Samples that are heterozygous or heterogeneous for two alleles will hybridize to both of two alternative probes.

ASH markers may be used as dominant markers, where the presence or absence of only one allele is determined from hybridization or lack of hybridization by only one probe. The alternative allele may be inferred from a lack of hybridization. In examples, ASH probe and target molecules may be RNA or DNA molecules; a target molecule may comprise any length of nucleotides beyond the sequence that is complementary to the probe; the probe may be designed to hybridize with either strand of a DNA target; and the size of the probe may be varied to conform with the requirements of different hybridization conditions.

Amplified variable sequences refer to amplified sequences of the plant genome that exhibit high nucleic acid residue variability between members of the same species. All organisms have variable genomic sequences, and each organism (with the exception of a clone) has a different set of variable sequences. Once identified, the presence of specific variable sequence can be used to predict phenotypic traits. DNA from a plant may in some examples be used as a template for amplification with primers that flank a variable sequence of DNA. The variable sequence may be amplified and then sequenced.

Self-sustained sequence replication may also and alternatively be used to identify genetic markers. Self-sustained sequence replication refers to a method of nucleic acid amplification using target nucleic acid sequences that are replicated exponentially in vitro under substantially isothermal conditions, using three enzymatic activities involved in retroviral replication: reverse transcriptase; Rnase H; and a DNA-dependent RNA polymerase. Guatelli et al. (1990) Proc. Natl. Acad. Sci. USA 87:1874. By mimicking the retroviral strategy of RNA replication by means of cDNA intermediates, this reaction accumulates cDNA and RNA copies of the original target.

Data representing detected marker allele(s) may be transmitted (for example, electronically; and via infrared, wireless, or optical transmission) to a computer or computer-readable medium for analysis or storage.

For example, an amplification primer or amplification primer pair may be admixed with a genomic nucleic acid isolated from a first cotton plant or germplasm, wherein the primer or primer pair is complementary or partially complementary to at least a portion of a marker locus, and the primer or primer pair is capable of initiating DNA polymerization by a DNA polymerase using the cotton genomic nucleic acid as a template. The primer or primer pair (e.g., a primer or primer pair provided as one of SEQ ID NO:27 and their equivalents) is extended in a DNA polymerization reaction utilizing a DNA polymerase and a template genomic nucleic acid to generate at least one amplicon.

"Positional cloning" refers to a particular cloning procedure in which a target nucleic acid is identified and isolated by its genomic proximity to a marker. For example, a genomic nucleic acid clone may include all or part of two more chromosomal regions that are proximal to one another. If a marker can be used to identify the genomic nucleic acid clone from a genomic library, standard methods such as sub-cloning and/or sequencing may be used to identify and or isolate sub-sequences of the clone that are located near the marker.

Locus: As used herein, the term "locus" refers to a position on the genome that corresponds to a measurable characteristic (e.g., a trait) or polymorphism. A locus (e.g., an SNP locus) is defined by a probe that hybridizes to DNA contained within the locus.

Marker-assisted breeding: As used herein, the term "marker-assisted breeding" may refer to an approach to breeding directly utilizing MAS for one or more traits (e.g., RN resistance). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Probe: In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}$P. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) *Proc. Natl. Acad. Sci. USA* 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait (e.g., RN resistance). For example, in some embodiments, a noncontiguous probe may be located within about 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker set forth in Tables 2-4 (e.g., a QTL marker set forth in Tables 3-4).

A probe may be an exact copy of a marker to be detected. A probe may also be a nucleic acid molecule comprising, or consisting of, a nucleotide sequence which is substantially identical to a cloned segment of the subject organism's (e.g., cotton) chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to a reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, N.Y., 1995.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters; transcription signals; and/or vector sequences. Any of the probes discussed, supra, may be used to define additional markers that are linked to a gene involved in RN resistance in cotton, and markers thus identified may be equivalent to exemplary markers named in the present disclosure, and thus are within the scope of the invention.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Exogenous: An "exogenous" molecule is a molecule that is not native to a specified system (e.g., a germplasm, variety, elite variety, and/or plant) with respect to nucleotide sequence and/or genomic location for a polynucleotide, and with respect to amino acid sequence and/or cellular localization for a polypeptide. In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Recombinant: The term "recombinant" refers to a material (e.g., recombinant nucleic acid, recombinant gene, recombinant polynucleotide, and/or recombinant polypeptide) that has been altered by human intervention. For example, the arrangement of the parts or elements of a recombinant molecule may not be a native arrangement, and/or the primary sequence of the recombinant molecule may been changed from its native sequence in some way. A material may be altered to produce a recombinant material within or removed from its natural environment or state. An open reading frame of a nucleic acid is recombinant if the nucleotide sequence of the open reading frame has been removed from its natural context and cloned into any type of artificial nucleic acid (e.g., a vector). Protocols and reagents to produce recombinant molecules, especially recombinant nucleic acids, are common, and their use is routine in the art. The term "recombinant" may also herein refer to a cell or organism that comprises recombinant material (e.g., a plant and/or plant cell that comprises a recombinant nucleic acid). In some examples, a recombinant organism is a transgenic organism.

As used herein, the term "introduced," when referring to translocation of a heterologous or exogenous nucleic acid into a cell, refers to the incorporation of the nucleic acid into the cell using any methodology available in the art. This term encompasses nucleic acid introduction methods including, for example and without limitation, transfection; transformation; and transduction.

As used herein, the term "vector" refers to a polynucleotide or other molecule that is capable of transferring at least one nucleic acid segment(s) into a cell. A vector may optionally comprise components/elements that mediate vector maintenance and enable its intended use (e.g., sequences necessary for replication, genes imparting drug or antibiotic resistance, a multiple cloning site, and/or operably-linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably-linked elements to facilitate cloning or subcloning steps (e.g., a multiple cloning site containing multiple restriction endonuclease sites).

The term "expression vector," as used herein, refers to a vector comprising operably-linked polynucleotide sequences that may facilitate expression of a coding sequence in a particular host organism. For example, a bacterial expression vector may facilitate expression of a coding sequence in a bacterium. A plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) comprise promoters, enhancers, termination, and polyadenylation signals (and other sequences) that are generally different from those used in prokaryotic expression vectors.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to RN resistance are SNP markers. Recent high-throughput genotyping technologies such as GoldenGate® and INFINIUM® assays (Illumina, San Diego, Calif.) may be used in accurate and quick genotyping methods by multiplexing SNPs from 384-plex to >100,000-plex assays per sample. Although SNP markers are highly useful, availability of high quality DNA sequence information is necessary for their discovery.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) *Nature* 409:928-33.

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term "cotton plant" may refer to, for example and without limitation, a whole cotton plant; multiple cotton plants; cotton plant cell(s); cotton plant protoplast; cotton tissue culture (e.g., from which a cotton plant can be regenerated); cotton plant callus; cotton plant parts (e.g., cotton seed, cotton flower, cotton cotyledon, cotton leaf, cotton stem, cotton bud, cotton root, and cotton root tip); and cotton plant cells that are intact in a cotton plant or in a part of a cotton plant.

A "transgenic plant" is a plant comprising within at least one of its cells an exogenous polynucleotide. In examples, the exogenous polynucleotide is stably-integrated within the genome of the cell, such that the polynucleotide may be inherited in successive generations. In some examples, the exogenous polynucleotide may be integrated into the genome as part of a recombinant expression cassette. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci. A "subline" may refer to an inbred subset of descendants from a common progenitor that are genetically distinct from other similarly inbred subsets descended from the same progenitor. In some embodiments, a "subline" may be produced by inbreeding seed from an individual cotton plant selected at the $F_3$ to $F_5$ generation until the residual segregating loci are homozygous across most or all loci.

Commercial cotton varieties are typically produced by aggregating the self-pollinated progeny ("bulking") of a single $F_3$ to $F_5$ plant from a controlled cross between 2 genetically different parents. While such a variety typically appears uniform, a self-pollinating variety derived from the selected plant eventually (for example, by the $F_8$ generation) becomes a mixture of homozygous plants that may vary in genotype at any locus that was heterozygous in the originally selected $F_3$ to $F_5$ plant. In embodiments described herein, marker-based sublines that differ from each other based on qualitative marker polymorphism at the DNA level at one or more specific loci, are produced by genotyping a sample of seed derived from individual self-pollinated progeny derived from a selected $F_3$ to $F_5$ plant. Such a seed sample may be genotyped directly as seed, or as plant tissue grown from seed. In some examples, seed sharing a common genotype at one or more specified marker locus are bulked to produce a subline that is genetically homogenous at one or more locus that is linked to a trait of interest (e.g., RN resistance).

An "elite line" or "elite strain" refers to an agronomically superior line that has been bred and selected (often through many cycles) for superior agronomic performance. Numerous elite cotton lines are available and known to those of skill in the art. An elite population is an assortment of elite lines or individuals from elite lines that may be used to represent the state of the art in terms of the available agronomically superior genotypes of a given crop species (e.g., cotton). Similarly, an elite germplasm or elite strain of germplasm is an agronomically superior germplasm. An elite germplasm may be obtained from a plant with superior agronomic performance, and may capable of being used to generate a plant with superior agronomic performance, such as a cotton of an existing or newly-developed elite line.

In contrast to elite lines, an "exotic line" or "exotic strain" (or an "exotic germplasm") refers to a line or germplasm obtained from a cotton not belonging to an available elite cotton line or strain of germplasm. In the context of a cross between two cotton plants or germplasms, an exotic germplasm is not closely related by descent to the elite germplasm with which it is crossed. Most commonly, exotic germplasm has been selected to introduce a novel genetic element (e.g., an allele form of interest) into a breeding program.

An "ancestral line" refers to a parent line that is or has been used as a source of genetic material, for example, for the development of elite lines. An "ancestral population" refers to a group of ancestors that have contributed the bulk of the genetic variation that was used to develop an elite line. "Descendants" are progeny of ancestors, and descendants may be separated from their ancestors by many generations of breeding. For example, elite lines are the descendants of their ancestors. A pedigree may be used to describe the relationship between a descendant and each of its ancestors. A pedigree may span one or more generations, and thus may describe relationships between a descendant and its ancestors removed by 1, 2, 3, 4, or more generations.

Trait or phenotype: The terms "trait" and "phenotype" are used interchangeably herein to refer to a measurable or observable heritable characteristic. A phenotype may in some examples be directly controlled by a single gene or genetic locus (i.e., a single gene trait). In other examples, a phenotype may be the result of an interaction between several genes (a complex trait). Thus, a QTL can act through a single gene mechanism or by a polygenic mechanism. In some examples, a trait or phenotype can be assigned a "phenotypic value," which corresponds to a quantitative value measured for the phenotypic trait.

The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Trait or phenotype: The terms "trait" and "phenotype" are used interchangeably herein. For the purposes of the present disclosure, traits of particular interest include agronomically important traits, as may be expressed, for example, in a crop plant.

Reniform nematode (RN) resistance: For the purposes of the present disclosure, a trait of particular interest is "reniform nematode resistance." Whether a particular cotton plant or germplasm comprises RN resistance may be determined by any of several methods known in the art, for example, an assay that measures RN reproduction in one or more of the plants or plants of the germplasm.

IV. Markers for Reniform Nematode Resistance in Cotton

Embodiments of the invention include markers that are linked to reniform nematode resistance, for example, in cotton produced by a cross of a tetraploid *Gossypium barbadense* genotype Inca Cotton GB713 and *G. hirsutum*. Such markers may be used, for example and without limitation, to identify cotton plants and germplasm having an increased likelihood of comprising an RN resistance phenotype; to select such cotton plants and germplasm (e.g., in a marker-assisted selection program); and to identify and select cotton plants and germplasm that do not have an increased likelihood of comprising an RN resistance phenotype. Use of one or more of the markers describe herein may provide advantages to plant breeders with respect to the time, cost, and labor involved in cotton breeding, when compared to currently available compositions and methods in the art. For example, one or more of the markers described herein may provide superior results in marker-assisted breeding of RN resistance in cotton, when compared to currently available markers for this purpose.

Disclosed herein are particular markers identified to be within or near an RN resistance major QTL region on chromosome 21 in the cotton genome that are polymorphic in parent genotypes. Among such QTL markers are particular marker alleles that are linked to an RN resistance phenotype in cotton. In some embodiments, a QTL marker that is linked to an RN resistance phenotype in cotton is selected from the subset of markers provided in Tables 2-4. For example and without limitation, a major QTL marker that is linked to an RN resistance phenotype in cotton may be selected from DASCTP_4812_64; DASCTP_6004646; DASCTP_60046_472; DCTE1_26139_678; DCTE1_278814_262; DCTE1_214911_694; DCTE1_233925_865; DCTE1_232591_126; DCTE1_365870_69; DASCTP_39375_356; DCTE1_240643_347; DCTE1_208529_965; DCTE1_271930_223; DASCTP_59246_191; DASCTP_28910_164; BNL3279; DASCTP_1656_527; DASCTP_51689_504; BNL4011; DCTE1_214869_124; DASCTP_8602_496; DASCTP_8602_418; GH132; and DASCTP_10515_556.

Mapping populations may be used to determine a marker that is linked to RN resistance. In some embodiments, such a mapping population may be derived from a cross of GB 713× an RN-sensitive Upland variety, though other populations may also and alternatively be used. Any of many suitable software platforms may be used to determine a linked marker locus. For example and without limitation, WINDOWS® QTL cartographer, TASSEL®; GENEFLOW®; and MAPMANAGER-QTX® may be used in particular examples. In some embodiments, such as when software is used in a linkage analysis, data reflecting detected allele information may be electronically transmitted or electronically stored during use or prior to use, for example, in a computer readable medium.

In some embodiments, a first cotton plant or germplasm that is likely to comprise an RN resistance phenotype is identified by detecting a plurality of marker alleles in the first cotton plant or germplasm. For example and without limitation, particular embodiments include methods for identifying plants or germplasm that is likely to comprise an RN resistance phenotype, where a marker allele linked to RN resistance is detected from among the molecular markers, DASCTP_4812_64; DASCTP_60046_46; DASCTP_60046_472; DCTE1_261396_78; DCTE1_278814_262; DCTE1_214911_694; DCTE1_233925_865; DCTE1_232591_126; DCTE1_365870_69; DASCTP_39375_356; DCTE1_240643_347; DCTE1_208529_965; DCTE1_271930_223; DASCTP_59246_191; DASCTP_28910_164; BNL3279; DASCTP_1656_527; DASCTP_51689_504; BNL4011; DCTE1_214869_124; DASCTP_8602_496; DASCTP_8602_418; GH132; DASCTP_10515_556; and their equivalents.

Methods for identifying plants or germplasm that is likely to comprise an RN resistance phenotype according to some embodiments comprise detecting more than one marker allele linked to low RN resistance from among such molecular markers. Particular embodiments include methods for identifying a plant or germplasm that is likely to comprise an RN resistance phenotype, where a marker allele is detected from among molecular markers that are linked to at least one marker linked to RN resistance selected from such markers.

In some embodiments, a detected allele is an allele form that positively correlates with RN resistance. Alternatively, an allele that is detected may be an allele form that negatively correlates with RN resistance, in which case the allele may be counter-selected. In the case where more than one marker allele is selected for detection, an allele is selected for each of the markers; thus, two or more alleles are detected. In some examples, a marker may comprise more than one advantageous (e.g., positively correlated) allele form; in such an example, any of such advantageous allele forms can be detected.

Thus, a plurality of marker alleles may be simultaneously detected in a single plant, germplasm, or population of plants. In examples of such methods, a plant or germplasm may be selected that contains positively correlated alleles from more than one marker linked to RN resistance. In particular examples, positively correlated alleles from more than one marker linked to RN resistance may be introgressed into a target (e.g., recipient) cotton germplasm. It will be appreciated by those of skill in the art that the simultaneous selection (and/or introgression) of positively correlated alleles from more than one RN resistance QTL marker in the same plant or germplasm may result in an additive (e.g., synergistic) phenotype in the plant or germplasm.

Although particular marker alleles may co-segregate with an RN resistance phenotype, such marker loci are not necessarily part of a QTL locus contributing to (e.g., responsible for) the RN resistance. For example, it is not a requirement that a co-segregating marker be comprised within a gene (e.g., as part of the gene open reading frame) that contributes to or imparts RN resistance. The association between a specific marker allele with an RN resistance phenotype may be due to the original "coupling" linkage phase between the co-segregating marker allele and a RN resistance QTL allele in the ancestral cotton line from which the RN resistance allele originated.

When referring to the relationship between two genetic elements (e.g., a genetic element contributing to RN resistance and a proximal marker), "coupling" phase linkage refers to the circumstance where the positively correlated allele at an RN resistance QTL is physically associated on the same chromosome strand as the positively correlated allele of the respective linked marker locus. In "coupling phase," both alleles are inherited together by progeny that inherit that chromosome strand. In "repulsion" phase linkage, the positively correlated allele at a locus of interest (e.g., a QTL for RN resistance) is physically linked with a normally negatively correlated allele at the proximal marker locus, and thus the two alleles that are normally positively correlated are not inherited together (i.e., the two loci are "out of phase" with each other).

As used herein, a "positively correlated" allele of a marker is that allele of the marker that co-segregates with a desired phenotype (e.g., RN resistance) in the mapping populations described herein. However, in view of the foregoing, it will be understood that due to the possibility of repulsion phase linkage, other allele forms of the marker may be used equivalently in other embodiments involving different populations.

Similarly, a linked marker allele form that does not co-segregate with RN resistance may also and alternatively be used in some embodiments, since such an allele form may be used to identify a plant that is not likely to comprise an RN resistance phenotype. For example, such an allele may be used for exclusionary purposes (e.g., counter-selection) during breeding to identify alleles that negatively correlate with RN resistance, and/or to eliminate RN susceptible plants or germplasm from subsequent rounds of breeding.

A QTL marker has a minimum of one positively correlated allele, although in some examples, the QTL marker may have two or more positively correlated alleles found in the population. Any positively correlated allele of such a marker may be used, for example, for the identification and construction of RN resistant cotton lines. In some examples, one, two, three, or more positively correlated allele(s) of different markers linked to RN resistance are identified in (or introgressed into) a plant, and all or a subset of the positively correlated markers may be selected for or against during MAS. In some embodiments, at least one plant or germplasm is identified that has at least one such allele that positively correlates with an RN resistance phenotype.

Marker loci are themselves traits, and may thus be analyzed according to standard linkage analysis, e.g., by tracking the marker loci during segregation. Therefore, in some embodiments, linkage between markers is determined, for example, where one cM is equal to a 1% chance that a first marker locus will be separated by crossing-over in a single generation from a second locus (which may be any other trait, (e.g., a second marker locus), or another trait locus that comprises or is comprised within a QTL).

Genetic markers that are linked to QTL markers (e.g., QTL markers provided in Tables 2-4 and their equivalents) are particularly useful when they are sufficiently proximal (i.e., sufficiently tightly linked) to a given QTL marker, so that the genetic marker and the QTL marker display a low recombination frequency. In some embodiments, a linked marker and a QTL marker display a recombination frequency of about 10% or less (i.e., the given marker is within about 10 cM of the QTL). By definition, these linked loci will co-segregate at least 90% of the time. Indeed, the closer a marker is to a QTL marker, the more effective and advantageous that marker becomes as an indicator for the desired trait. Nonetheless, markers that are, for example, more than about 10 cM from a QTL may be useful, particularly when combined with other linked markers.

Thus, in some embodiments, linked loci such as a QTL marker locus and a second marker locus display an interlocus recombination frequency of about 10% or less; for example and without limitation, about 9% or less, about 8% or less, about 7% or less, about 6% or less, about 5% or less, about 4% or less, about 3% or less, and about 2% or less. In some examples, the relevant loci (e.g., a marker locus and a target locus, such as a QTL) display a recombination a frequency of about 1% or less; for example and without limitation, about 0.75% or less, about 0.5% or less, and about 0.25% or less. Thus, loci may in particular embodiments be separated by about 10 cM; about 9 cM; about 8 cM; about 7 cM; about 6 cM; about 5 cM; about 4 cM; about 3 cM; about 2 cM; about 1 cM; about 0.75 cM; about 0.5 cM; about 0.25 cM; or less. In some examples, specific linked markers may be determined by review of a genetic map of the cotton genome.

In some aspects, linkage may be expressed as a recombination frequency limit, or as a genetic or physical distance range. For example, in some embodiments, two linked loci are two loci that are separated by less than 50 cM map units. In some examples, linked loci are two loci that are separated by less than 40 cM. In some examples, two linked loci are two loci that are separated by less than 30 cM. In some examples, two linked loci are two loci that are separated by less than 25 cM. In some examples, two linked loci are two loci that are separated by less than 20 cM. In some examples, two linked loci are two loci that are separated by less than 15 cM. In some examples, linkage may be expressed as a range with an upper and a lower limit; for example and without limitation, between about 10 and 20 cM; between about 10 and 30 cM; between about 10 and 40 cM; between about 0.5 and about 10 cM; between about 0.1 and about 9 cM; between about 0.1 and about 8 cM; between about 0.1 and about 7 cM; between about 0.1 and about 6 cM; between about 0.1 and about 5 cM; between about 0.1 and about 4 cM; between about 0.1 and about 3 cM; between about 0.1 and about 2 cM; between about 0.1 and about 1 cM; and between about 0.1 and about 0.5 cM.

Markers described herein (e.g., those markers set forth in Tables 2-4, and markers linked to at least one of the foregoing) are positively correlated with RN resistance in some embodiments. Thus, these markers may be sufficiently proximal to an RN resistance QTL and/or trait that one or more of the markers may be used as a predictor for an RN resistance trait. This predictive ability is extremely useful in the context of MAS, as discussed in more detail herein.

Use of particular markers described herein that are linked to an RN resistance phenotype and/or QTL marker is not necessarily restricted to any particular cotton genetic map or methodology. It is noted that lists of linked markers may vary between maps and methodologies due to various factors. For example, the markers that are placed on any two maps may not be identical, and a first map may have a greater marker density than another, second map. Also, the mapping populations, methodologies, and algorithms used to construct genetic maps may differ. One of skill in the art recognizes that one genetic map is not necessarily more or less accurate than another, and the skilled person furthermore recognizes that any cotton genetic map may be used to determine markers that are linked to a particular marker. For example, particular linked markers can be determined from any genetic map known in the art (e.g., an experimental map or an integrated map), and can be determined from any new mapping dataset.

Embodiments of the present invention are not limited to any particular cotton population or use of any particular methodology (e.g., any particular software or any particular set of software parameters) to identify or determine linkage of a particular marker with an RN resistance phenotype. In view of the present disclosure, one of ordinary skill in the art will be able to extrapolate features of the markers described herein to any cotton gene pool or population of interest, and use any particular software and software parameters in so doing.

V. Detection of Markers for Reniform Nematode Resistance in Cotton

Methods for detecting (identifying) cotton plants or germplasm that carry particular alleles of RN resistance marker loci are a feature of some embodiments. In some embodiments, any of a variety of marker detection protocols available in the art may be used to detect a marker allele, depending on the type of marker being detected. In examples, suitable methods for marker detection may include amplification and identification of the resulting amplified marker by, for example and without limitation, PCR; LCR; and transcription-based amplification methods (e.g., ASH, SSR detection, RFLP analysis, and many others).

In general, a genetic marker relies on one or more property of nucleic acids for its detection. For example, some techniques for detecting genetic markers utilize hybridization of a probe nucleic acid to a nucleic acid corresponding to the genetic marker (e.g., an amplified nucleic acid produced using a genomic cotton DNA molecule as a template). Hybridization formats including, for example and without limitation, solution phase; solid phase; mixed phase; and in situ hybridization assays may be useful for allele detection in particular embodiments. An extensive guide to the hybridization of nucleic acids may be found, for example, in Tijssen (1993) *Laboratory Techniques in Biochemistry and Molecular Biology—Hybridization with Nucleic Acid Probes* Elsevier, N.Y.

Markers corresponding to genetic polymorphisms between members of a population may be detected by any of numerous methods including, for example and without limitation, nucleic acid amplification-based methods; and nucleotide sequencing of a polymorphic marker region. Many detection methods (including amplification-based and sequencing-based methods) may be readily adapted to high throughput analysis in some examples, for example, by using available high throughput sequencing methods, such as sequencing by hybridization.

Amplification primers for amplifying SSR-type marker loci are included in particular examples of some embodiments. Tables 3-4 provide specific primers and primer pairs for amplification of particular markers described herein. However, one of skill will immediately recognize that other sequences on either side of the given primers may be used in place of the given primers, so long as the primers are capable of amplifying a nucleotide sequence comprising the allele to be detected. Further, the precise probe used for allele detection may vary. For example, any probe capable of identifying the region of a marker amplicon to be detected may be substituted for the exemplary probes listed herein. Further, the configuration of amplification primers and detection probes may also vary. Thus, embodiments are not limited to the primers and probes specifically recited herein. Although many specific examples of primers are provided herein (see Tables 3-4), suitable primers to be used with the invention may be designed using any suitable method. For example, equivalent primers may be designed using any suitable software program, such as for example and without limitation, LASERGENE®.

Molecular markers may be detected by established methods available in the art including, for example and without limitation: ASH, or other methods for detecting SNPs; AFLP detection; amplified variable sequence detection; RAPD detection; RFLP detection; self-sustained sequence replication detection; SSR detection; SSCP detection; and isozyme markers detection. While the exemplary markers provided in Tables 2-4 are SNP and SSR markers, any of the aforementioned marker types may be employed in particular embodiments to identify chromosome segments encompassing a genetic element that contributes to an RN resistance phenotype in cotton.

For example, markers that comprise RFLPs may be detected, for example, by hybridizing a probe (which is typically a sub-fragment or synthetic oligonucleotide corresponding to a sub-fragment) of the nucleic acid to be detected to restriction-digested genomic DNA. The restriction enzyme is selected so as to provide restriction fragments of at least two alternative (or polymorphic) lengths in different individuals or populations. Determining one or more restriction enzyme(s) that produces informative fragments for each cross is a simple procedure that is easily accomplished by those of skill in the art after provision of the target DNA sequence. After separation by length in an appropriate matrix (e.g., agarose or polyacrylamide) and transfer to a membrane (e.g., nitrocellulose or nylon), a labeled probe may be hybridized under conditions that result in equilibrium binding of the probe to the target, followed by removal of excess probe by washing, and detection of the labeled probe.

In some embodiments, an amplification step is utilized as part of a method to detect/genotype a marker locus. However, an amplification step is not in all cases a requirement for marker detection. For example, an unamplified genomic DNA may be detected simply by performing a Southern blot on a sample of genomic DNA. Separate detection probes may also be omitted in amplification/detection methods, for example and without limitation, by performing a real time amplification reaction that detects product formation by modification of an amplification primer upon incorporation into a product; incorporation of labeled nucleotides into an amplicon; and by monitoring changes in molecular rotation properties of amplicons as compared to unamplified precursors (e.g., by fluorescence polarization).

PCR, RT-PCR, real-time PCR, and LCR are in particularly broad use as amplification and amplification-detection methods for amplifying and detecting nucleic acids (e.g., those comprising marker loci). Details regarding the use of these and other amplification methods can be found in any of a variety of standard texts including, for example, Sambrook et al., *Molecular Cloning—A Laboratory Manual* (2000) 3rd Ed., Vol. 1-3, Cold Spring Harbor Laboratory, Cold Spring Harbor, N.Y.; *Current Protocols in Molecular Biology* (supplemented through 2002) F. M. Ausubel et al., eds., *Current Protocols*, a joint venture between Greene Publishing Associates, Inc. and John Wiley & Sons, Inc.; and *PCR Protocols A Guide to Methods and Applications* (1990) Innis et al. eds) Academic Press Inc., San Diego, Calif. Additional details regarding detection of nucleic acids in plants can also be found, for example, in *Plant Molecular Biology* (1993) Croy (ed.) BIOS Scientific Publishers, Inc.

Additional details regarding techniques sufficient to direct persons of skill through particular in vitro amplification and detection methods, including the polymerase chain reaction (PCR), the ligase chain reaction (LCR), Qβ-replicase amplification, and other RNA polymerase-mediated techniques (e.g., NASBA), and examples thereof, may also be found in, for example: U.S. Pat. No. 4,683,202; Arnheim and Levinson (1991) *J. NIH Res.* 3:81-94; Kwoh et al. (1989) *Proc. Natl. Acad. Sci. USA* 86:1173; Guatelli et al. (1990), supra; Lomeli et al. (1989) *J. Clin. Chem.* 35:1826; Landegren et al. (1988) *Science* 241:1077-80; Van Brunt (1990) *Biotechnology* 8:291-4; Wu and Wallace (1989) *Gene* 4:560; Barringer et al. (1990) *Gene* 89:117; and Sooknanan and Malek (1995) *Biotechnology* 13:563-4. Improved methods of amplifying large nucleic acids by PCR, which may be useful in some applications of positional cloning, are further described in Cheng et al. (1994) *Nature* 369:684, and the references cited therein, in which PCR amplicons of up to 40 kb are generated.

Many available biology texts also have extended discussions regarding PCR and related amplification methods. One of skill will appreciate that essentially any RNA can be converted into a double-stranded DNA that is suitable for restriction digestion, PCR amplification, and sequencing using reverse transcriptase and a polymerase (e.g., by RT-PCR).

In some embodiments, a nucleic acid probe may be used to detect a nucleic acid that comprises a marker allele nucleotide sequence. Such probes can be used, for example, in positional cloning to isolate nucleotide sequences that are linked to a marker allele sequence. Nucleic acid probes that are useful in particular embodiments are not limited by any particular size constraint. In some embodiments, a nucleic acid probe may be, for example and without limitation, at least 20 nucleotides in length; at least 50 nucleotides in length; at least 100 nucleotides in length; and at least 200 nucleotides in length. Nucleic acid probes to a marker locus may be cloned and/or synthesized.

Any suitable label may be used with a probe in particular examples. Detectable labels suitable for use with nucleic acid probes include any composition detectable by spectroscopic, radioisotopic, photochemical, biochemical, immunochemical, electrical, optical, or chemical means. Thus, a hybridized probe may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, and colorimetric labels. Other labels include ligands that bind to antibodies or specific binding targets labeled with fluorophores, chemiluminescent agents, and enzymes. A probe may also comprise radiolabelled PCR primers that are used to generate a radiolabeled amplicon. Additional information regarding labeling strategies for labeling nucleic acids, and corresponding detection strategies may be found, for example, in Haugland (1996) *Handbook of Fluorescent Probes and Research Chemicals*, Sixth Edition, Molecular Probes, Inc., Eugene Oreg.; and Haugland (2001) *Handbook of Fluorescent Probes and Research Chemicals, Eighth Edition*, Molecular Probes, Inc., Eugene, Oreg. (Available on CD ROM). In particular examples, PCR detection and quantification is carried out using dual-labeled fluorogenic oligonucleotide probes, for example, TAQMAN® probes (Applied Biosystems).

In some embodiments, primers are not labeled, and marker PCR amplicons may be visualized, for example, following their size resolution (e.g., following agarose gel electrophoresis). In particular examples, ethidium bromide staining of PCR amplicons following size resolution allows visualization of differently size amplicons corresponding to different marker alleles.

Primers for use in embodiments are not limited to those capable of generating an amplicon of any particular size. For example, primers used to amplify particular marker loci and alleles are not limited to those amplifying the entire region of the relevant locus. The primers may generate an amplicon of any suitable length that is longer or shorter than those given in the allele definitions. In examples, marker amplification may produce an amplicon that is, for example and without limitation, at least 20 nucleotides in length; at least 50 nucleotides in length; at least 100 nucleotides in length; and at least 200 nucleotides in length.

Synthetic methods for making oligonucleotides and useful compositions comprising oligonucleotides (e.g., probes, primers, molecular beacons, PNAs, and LNAs) are generally well-known by those of skill in the art. For example, oligonucleotides may be synthesized chemically according to the solid phase phosphoramidite triester method described in, for example, Beaucage and Caruthers (1981) *Tetrahedron Letts.* 22(20):1859-62. Such methods may employ an automated synthesizer, for example and without limitation, as described in Needham-VanDevanter et al. (1984) *Nucleic Acids Res.* 12:6159-68. Oligonucleotides (including modified oligonucleotides) may also be ordered from a variety of commercial sources including, for example and without limitation, The Midland Certified Reagent Company; The Great American Gene Company; ExpressGen Inc.; and Operon Technologies Inc. Similarly, PNAs may be custom ordered from any of a variety of sources including, for example and without limitation, PeptidoGenic; HTI Bio-Products, Inc.; BMA Biomedicals Ltd (U.K.); and Bio.Synthesis, Inc.

In some embodiments, an in silico method may be used to detect a marker allele. For example, the sequence of a nucleic acid comprising a marker sequence may be stored in a computer. The desired marker locus sequence (or its homolog) may be identified using an appropriate nucleic acid search algorithm, as provided by, for example and without limitation, BLAST™, or even simple word processors.

In some embodiments, a marker allele is detected using a PCR-based detection method, where the size or sequence of a PCR amplicon comprising the marker is indicative of the absence or presence of a particular marker allele. In some examples, PCR primers are hybridized to conserved regions flanking the polymorphic marker region. PCR primers so used to amplify a molecular marker are sometimes referred to in the art as "PCR markers," or simply "markers."

A primary motivation for development of molecular markers in crop species is the potential for increased efficiency in plant breeding through marker assisted selection (MAS). Genetic markers that are linked to a trait or gene of interest may be used to identify plants that contain a desired marker allele at one or more loci, which plants are thus expected to transfer the desired marker allele, along with the trait or gene of interest, to their progeny. Genetic markers may be used to identify plants that contain a particular genotype at one locus, or at several unlinked or linked loci (e.g., a haplotype). Similarly, marker alleles described herein may be introgressed into any desired cotton genetic background, germplasm, plant, line, variety, etc., as part of an overall MAS breeding program designed to enhance cotton yield or generally improve a cotton variety.

According to some embodiments, markers described herein provide the means to identify cotton plants and germplasm that comprise RN resistance (or RN susceptibility) by identifying plants and germplasm comprising a specific allele at a locus such as those set forth in Tables 2-4, and a marker locus linked to at least one of the foregoing. By identifying plants lacking a marker allele that co-segregates with RN resistance, RN susceptible plants and germplasm (or plants with a lesser resistance to RN infestation and/or damage) may be identified, for example, for elimination from subsequent crosses and breeding.

According to the foregoing, embodiments of the invention include molecular markers that have a significant probability of co-segregation with a QTL that contributes to or imparts an RN resistance phenotype. These QTL markers find use in marker assisted selection for desired traits (RN resistance), and also have other uses. Embodiments of the invention are not limited to any particular method for the detection or analysis of these markers.

Comparison of DNA sequence information with available homologous sequences across species genotypes using data-mining and bioinformatic tools generally assists in SNP marker discovery. SNP marker development typically involves sequence comparison among homologous sequences or mapping to a reference genome, multiple sequence alignment, data-mining for SNP discovery, estimation of allelic frequency at putative SNP locations, and candidate SNP selection for validation. This process is relatively straightforward for diploid species with low genetic complexity. However, the rate of false positive SNP detection increases with higher genomic complexity, genome size, and available sequence information.

For example, several plant species (e.g., cotton) have evolved over time to have multiple haploid sets of chromosomes in their nuclear genome, thus contributing to the development of a polyploid plant species. These polyploid species can be further categorized into autopolyploids (i.e., those having similar sets of multiple haploid genomes (e.g., "AAAA")) and allopolyploids (i.e., those having multiple sets of different sub-genomes (e.g., "AADD")). Cotton is an allotetraploid, with A and D sub-genomes. Thus, SNP discovery is highly challenging in this tetraploid crop species, due to its polyploidy, high genome complexity, and large genome size. Tetraploid cotton has a 2500 MB genome with 52 chromosomes that are distributed equally with 13 pairs in both A and D genomes. Hendrix & Stewart (2005) *Ann. Bot.* 95(5):789-97.

SNP detection programs, such as AutoSNP (Batley et al. (2003) *Plant Physiol.* 132:84-91), typically use allelic frequency as a measure for identifying candidate SNPs. However, this measure alone may not be reliable for polyploids (e.g., cotton), due to the high abundance of paralogous sequences in the genome that in turn result in a high false positive SNP detection rate. This necessitates development of a new robust SNP detection pipeline that can be used for large and highly complex genomes with reduced risk of false SNP detection rate.

In view of the foregoing, to increase the efficiency of SNP detection from homologous sequences, and reduce the risk of high false positive rate due to homeologous genomes in cotton and canola, some embodiments utilize a "HAPSNP" pipeline. In particular embodiments, sequence contigs generated at high stringency may be searched for putative SNPs, thereby used to generate haplotype and allelic frequency in different cotton genotypes (e.g., genotypes from different Gossypium species or within the species), to discriminate paralogous/homeologous SNPs from homologous SNPs. A haplotype clustering pipeline may utilize an assembly algorithm (e.g., CAP3; Huang & Madan (1999) *Genome Res.* 9(9):868-77), an SNP mining algorithm (e.g., QualitySNP; Tang et al. (2006) *BMC Bioinformatics* 7(1):438) as part of SNP calling module, a SNP filteration module, a haplotype calling module and a SNP sequence formatting module. Sequences generated from *G. hirsutum* and *G. barbadense* genotypes were used to demonstrate this pipeline.

In a haplotype clustering pipeline, SNPs may be classified as (1) true SNPs from a single locus; (2) SNPs that are heterologous in one genotype and homologous in other genotype; and (3) as SNPs that are paralogous/homeologous within each genotype. True SNP markers and SNPs that are heterologous in one genotype and homologous in other genotype may be selected for utilization for genotyping and mapping purposes. Contig information may be used to generate SNP markers with flanking sequence information for direct use in assay design with high-throughput genotyping platforms, for example and without limitation, GOLDENGATE® and INFINIUM® (Illumina) assays. In some examples, HAPSNP pipeline may achieve a higher validation rate, due at least in part to its efficiency in classifying the foregoing three different types of SNPs in silico.

VI. Introgression of Markers for Reniform Nematode Resistance into Cotton

As set forth, supra, identification of cotton plants or germplasm that includes a marker allele or alleles that is/are linked to an RN resistance phenotype provides a basis for performing marker assisted selection of cotton. In some embodiments, at least one cotton plant that comprises at least one marker allele that is positively correlated with RN resistance is selected, while cotton plants that comprise marker alleles that are negatively correlated with RN resistance may be selected against.

Desired marker alleles that are positively correlated with RN resistance may be introgressed into cotton having a particular (e.g., elite) genetic background, so as to produce an introgressed RN resistant cotton plant or germplasm. In some embodiments, a plurality of RN resistance markers may be sequentially or simultaneous selected and/or introgressed into cotton. The particular combinations of RN resistance markers that may be selected for in a single plant or germplasm is not limited, and can include a combination of markers such as those set forth in Tables 2-4; a subset of the markers set forth in Tables 2-4; any markers linked to the markers set forth in Tables 2-4; or any markers located within the QTL intervals defined herein on cotton chromosome 21.

In embodiments, the ability to identify QTL marker alleles that are positively correlated with RN resistance of a cotton plant provides a method for selecting plants that have favorable marker loci as well. For example, any plant that is identified as comprising a desired marker allele (e.g., a marker allele that positively correlates with RN resistance) may be selected for, while plants that lack the allele (or that comprise an allele that negatively correlates with RN resistance) may be selected against. Thus, in particular embodiments, subsequent to identification of a marker allele in a first plant or germplasm, an introgression method includes selecting the first cotton plant or germplasm, or selecting a progeny of the first cotton plant or germplasm. In some examples, the resulting selected cotton plant or germplasm may be crossed with a second cotton plant or germplasm (e.g., an elite cotton), so as to produce progeny comprising the marker allele and desirable characteristics and/or alleles of the second plant or germplasm.

In some embodiments, a method of introgressing an RN resistance QTL may include, for example, providing at least one marker linked to RN resistance (e.g., a marker that co-segregates with RN resistance); determining the marker allele in a first cotton plant or germplasm comprising a RN resistance QTL; and introgressing the marker allele into a second cotton plant or germplasm, so as to produce an introgressed cotton plant or germplasm. In particular embodiments, the second cotton plant or germplasm may be susceptible to RN infection and/or damage as compared to the first cotton plant or germplasm, while the introgressed cotton plant or germplasm will comprise RN resistance as compared to the second plant or germplasm. As discussed in more detail below, an introgressed cotton plant or germplasm produced by these and other embodiments are also included in embodiments of the invention.

In some embodiments, where an introgressed cotton plant or germplasm is produced by any of the methods provided herein, the introgressed cotton plant or germplasm may be characterized by the capacity of the plant or germplasm to support reniform nematode infection and/or reproduction. For example and without limitation, an introgressed plant or germplasm may comprise, about 6 weeks after inoculating the plant with ~2,000 adult and juvenile reniform nematodes, from 138 to 24,806 nematodes. The resulting RN count may be used to classify the resistance level as highly resistant (<250 RN), resistant (>251 and <1500 RN), moderately resistant (>1501 and <9200 RN) and susceptible (>9200 RN).

In addition to introgressing selected marker alleles (e.g., through standard breeding methods) into desired genetic backgrounds, so as to introgress an RN resistance QTL into the background, transgenic approaches may be used in some embodiments to produce RN resistant cotton plants and/or germplasm. In some embodiments, an exogenous nucleic acid (e.g., a gene or open reading frame) that is linked to at least one marker described herein in cotton may be introduced into a target plant or germplasm. For example, a nucleic acid coding sequence linked to at least one marker described herein may be cloned from cotton genomic DNA (e.g., via positional cloning) and introduced into a target plant or germplasm.

Thus, particular embodiments include methods for producing a cotton plant or germplasm comprising an RN resistance phenotype, wherein the method comprises introducing an exogenous nucleic acid into a target cotton plant or progeny thereof, wherein the exogenous nucleic acid is substantially identical to a nucleotide sequence that is linked to at least one positively-correlated marker allele at one or more marker locus that is linked to RN resistance. In some examples, the marker locus may be selected from those set forth in Tables 2-4 (e.g., those set forth in Tables 3-4) and a marker that is linked (e.g., demonstrating not more than 10% recombination frequency) to at least one of the foregoing. In some embodiments, a plurality of linked markers may be used to construct a transgenic plant. Which of the markers described herein that are used in such a plurality is within the discretion of the practitioner.

Any of a variety of methods can be used to provide an exogenous nucleic acid to a cotton plant or germplasm. In some embodiments, a nucleotide sequence is isolated by positional cloning, and is identified by linkage to a marker allele that is positively correlated with RN resistance. For example, the nucleotide sequence may correspond to an open reading frame (ORF) that encodes a polypeptide that, when expressed in a cotton plant, results in or contributes to the cotton plant having RN resistance. The nucleotide sequence may then be incorporated into an exogenous nucleic acid molecule. The precise composition of the exogenous nucleic acid may vary. For example, an exogenous nucleic acid may comprise an expression vector to provide for expression of the nucleotide sequence in the plant wherein the exogenous nucleic acid is introduced.

Markers linked to RN resistance may be introgressed (for example, thereby introgressing an RN resistance phenotype) into a cotton plant or germplasm utilizing a method comprising marker assisted selection. In embodiments, MAS is performed using polymorphic markers that have been identified as having a significant likelihood of co-segregation with an RN resistance trait. Such markers (e.g., those set forth in Tables 2-4) are presumed to map within or near a gene or genes that contribute to the RN resistance of the plant (compared to a plant comprising the wild-type gene or genes). Such markers may be considered indicators for the trait, and may be referred to as QTL markers. In embodiments, a plant or germplasm is tested for the presence of a positively correlated allele in at least one QTL marker.

In embodiments, linkage analysis is used to determine which polymorphic marker allele demonstrates a statistical likelihood of co-segregation with an RN resistance phenotype. Following identification of such a positively correlated marker allele for the RN resistance phenotype, the marker may then be used for rapid, accurate screening of plant lines for the RN resistance allele without the need to grow the plants through their life cycle and await phenotypic evaluations. Furthermore, the identification of the marker permits genetic selection for the particular RN resistance allele, even when the molecular identity of the actual RN resistance QTL is unknown. A small tissue sample (for example, from the first leaf of the plant) may be taken from a progeny cotton plant produced by a cross, and screened with the appropriate molecular marker. Thereby, it may be rapidly determined whether the progeny should be advanced for further breeding. Linked markers also remove the impact of environmental factors that may influence phenotypic expression, thereby allowing the selection for RN resistant cotton in an environmental neutral manner. Therefore, while the contributions of various environmental factors to the nematode susceptibility of plants may appear at first glance to confound the use of the markers described herein, in fact a particular advantage of these markers is that they do not depend on environment for their utility.

In some embodiments comprising MAS, a polymorphic QTL marker locus may be used to select a plant that contains a marker allele (or alleles) that is positively correlated with an RN resistance phenotype. For example, a nucleic acid corresponding to the marker nucleic acid allele may be detected in a biological sample from the plant to be selected. This detection may take the form of hybridization of a probe nucleic acid to a marker allele or amplicon thereof (e.g., using allele-specific hybridization, Southern analysis, northern analysis, in situ hybridization, and hybridization of primers followed by PCR amplification of a region of the marker). After the presence (or absence) of the particular marker allele in the biological sample is verified, the plant is selected, and may in some examples be used to make progeny plants by selective breeding.

RN resistance marker loci may be combined during cotton plant breeding with markers/genes for other desirable traits (e.g., high yield) to develop improved cotton varieties. Screening large numbers of samples by non-molecular methods (e.g., trait evaluation in cotton plants) is generally expensive, time consuming, and unreliable. Use of the polymorphic markers described herein, which are linked to an RN resistance QTL, provides an effective method for selecting desirable varieties in breeding programs. Advantages of marker-assisted selection over field evaluations for RN resistance include, for example, that MAS can be done at any time of year, regardless of the growing season. Moreover, as set forth, supra, environmental effects are largely irrelevant to marker-assisted selection.

When a population is segregating for multiple marker loci linked to one or more traits (e.g., multiple markers linked to RN resistance), the efficiency of MAS compared to phenotypic screening becomes even greater, because all of the marker loci may be evaluated in the lab together from a single sample of DNA. In particular embodiments of the invention, a plurality of markers set forth in Tables 2-4, as well as markers linked to at least one of the foregoing, may be assayed simultaneously or sequentially from a single sample, or from a plurality of parallel samples.

Another use of MAS in plant breeding is to assist the recovery of the recurrent parent genotype by backcross breeding. Backcrossing is usually performed for the purpose of introgressing one or a few markers or QTL loci from a donor parent (e.g., a parent comprising desirable RN resistance marker loci) into an otherwise desirable genetic background from a recurrent parent (e.g., an otherwise high yielding cotton line). The more cycles of backcrossing that are done, the greater the genetic contribution of the recurrent parent to the resulting introgressed variety. In some examples, many cycles of backcrossing may be carried out, for example, because RN resistant plants may be otherwise undesirable, e.g., due to low yield, low fecundity, etc. In contrast, strains which are the result of intensive breeding programs may have excellent yield, fecundity, etc., also being more resistant to RN infection and/or damage than the recurrent parent. In marker assisted backcrossing of specific markers from a donor source, which may or may not constitute an elite genetic background to an elite variety that will serve as the recurrent line, the practitioner may select among backcross progeny for the donor marker, and then use repeated backcrossing to the recurrent line to reconstitute as much of the recurrent line's genome as possible.

According to the foregoing, markers and methods described herein may be utilized to guide marker assisted selection or breeding of cotton varieties with the desired complement (set) of allelic forms of chromosome segments associated with superior agronomic performance (e.g., RN resistance, along with any other available markers for yield, disease resistance, etc.). Any of the described marker alleles may be introduced into a cotton line via introgression (e.g., by traditional breeding, via transformation, or both) to yield a cotton plant with superior agronomic performance. If nucleic acids from a plant are positive for a desired genetic marker allele, the plant may be self-fertilized in some embodiments to create a true breeding line with the same genotype, or it may be crossed with a plant comprising the same marker allele, or other desired markers and/or characteristics to create a sexually-crossed hybrid generation.

In some embodiments, a method of the present invention is applied to at least one related cotton plant such as from progenitor or descendant lines in the subject cotton plant's pedigree, such that inheritance of the desired RN resistance allele can be traced. The number of generations separating cotton plants being subjected to methods according to such embodiments may be, for example and without limitation, from 1 to 20; from 1 to 5; and 1, 2, or 3 generations of separation. For example, a direct descendant or parent of the cotton plant may be subject to the method (i.e., one generation of separation).

Genetic diversity is important in breeding programs. With limited diversity, the genetic gain achieved in a breeding program will eventually plateau when all of the favorable alleles have been fixed within the elite population. Therefore, one objective of plant breeding is to incorporate diversity into an elite pool without losing the genetic gain that has already been made, and with the minimum possible investment. MAS provide an indication of which genomic regions, and which favorable alleles from the original ancestors, have been selected for and conserved over time, facilitating efforts to incorporate favorable variation from exotic germplasm sources (parents that are unrelated to the elite gene pool) in the hopes of finding favorable alleles that do not currently exist in the elite gene pool. Thus, in some embodiments, markers described herein may be used for MAS in crosses involving (elite×exotic) cotton lines by subjecting segregating progeny to MAS to maintain major yield alleles, along with particular RN resistance marker alleles.

The molecular marker loci and alleles described herein (e.g., those set forth in Tables 2-4, and markers linked to at least one of the foregoing) may be used in some embodiments, as indicated previously, to identify a RN resistance QTL, which may then be cloned by familiar procedures. Such RN resistance clones may be first identified by their genetic linkage to markers described herein. For example, "positional gene cloning" takes advantage of the physical proximity of a RN resistance marker to define an isolated chromosomal fragment containing an RN resistance QTL gene. The isolated chromosomal fragment may be produced by such well-known methods as, for example and without limitation, digesting chromosomal DNA with one or more restriction enzymes, by amplifying a chromosomal region using PCR, and any suitable alternative amplification reaction. The digested or amplified fragment may subsequently be ligated into a vector suitable for replication and/or expression of the inserted fragment. Markers that are adjacent to an ORF associated with a phenotypic trait may be specifically hybridized to a DNA clone (e.g., a clone from a genomic DNA library), thereby identifying a clone on which the ORF (or a fragment of the ORF) is located. If a marker is more distant from the RN resistance QTL gene, a fragment containing the ORF may be identified by successive rounds of screening and isolation of clones, which together comprise a contiguous sequence of DNA. This process is commonly referred to as "chromosome walking," and it may be used to produce a "contig" or "contig map."

Protocols sufficient to guide one of skill through the isolation of clones associated with linked markers are found in, for example, Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989; and Ausubel et al., Eds., *Current Protocols in Molecular Biology*, Chapter 2, Greene Publishing and Wiley-Interscience, N.Y., 1995.

VII. Plants Comprising Markers for Reniform Nematode Resistance

Some embodiments include methods for making a cotton plant, and further include these cotton plants, per se. In particular embodiments, such a method may comprise crossing a first parent cotton plant comprising at least one marker allele that is positively correlated with RN resistance with a second cotton plant, to yield cotton plant progeny. Such cotton plant progeny may be assayed for marker alleles linked to RN resistance, and desired progeny may be selected. Such progeny plants, or seed thereof, may be subject to a variety of uses including, for example and without limitation, they may be sold commercially for cotton production; processed to obtain a desired cotton product (e.g., cotton fiber); and/or further utilized in subsequent rounds of breeding. Cotton plants according to some embodiments include progeny plants that comprise at least one of the allelic forms of the markers described herein, such that further progeny are capable of inheriting marker allele(s) linked to RN resistance.

Some embodiments include methods for producing a cotton plant comprising RN resistance (e.g., increased RN resistance when compared to a parent cotton plant). In particular embodiments, such methods may include production of such a plant by conventional plant breeding, or by introducing an exogenous DNA comprising an RN resistance QTL (e.g., a transgene) into a cotton variety or plant.

In particular embodiments, a method for producing a cotton plant comprising RN resistance may comprise introducing an RN resistance QTL from a *G. barbadense* germplasm into an Upland cotton comprising root knot nematode (RKN; *Meloidogyne incognita*) resistance. In some examples, the presence of RKN resistance in the cotton plant comprising an RN resistance QTL may synergistically increase the RN resistance of the cotton plant; i.e., the RN resistance phenotype observed in such plant may be more than the RN resistance of a similar cotton plant that does not comprise RKN resistance.

In some embodiments, a cotton plant comprising RN resistance may show a comparative resistance to reniform nematode infection and/or damage, when compared to a non-resistant control cotton plant. A control cotton plant may be genetically similar (e.g., it may have parent varieties in common with the cotton plant comprising RN resistance), except for the disease resistance allele or alleles in question. The comparative resistance of such plants may be assayed under similar conditions with equivalent, or near equivalent, exposure to reniform nematode infection.

Thus, some embodiments include host cells and organisms that are transformed with nucleic acids corresponding to an RN resistance QTL identified using at least one marker linked to RN resistance described herein. In some examples, such nucleic acids may include chromosome intervals (e.g., genomic fragments), ORFs, and/or cDNAs that encode expression products that contribute to an RN resistance phenotype in cotton.

Host cells may be genetically engineered (e.g., transduced, transfected, transformed, etc.) with a vector (e.g., a cloning vector, shuttle vector, or expression vector) that comprises an ORF linked to a marker of RN resistance. Vectors include, for example and without limitation, plasmids; phagemids; *Agrobacterium*; viruses; naked polynucleotides (linear or circular); and conjugated polynucleotides. Many vectors may be introduced into bacteria, especially for the purpose of propagation and expansion.

Vectors may be introduced into plant tissues, cultured plant cells, and plant protoplasts by any of a variety of standard methods known in the art including, for example and without limitation: electroporation (From et al. (1985) *Proc. Natl. Acad. Sci. USA* 82:5824); infection by viral vectors such as cauliflower mosaic virus (CaMV) (see, e.g., U.S. Pat. No. 4,407,956); ballistic penetration by small particles comprising the nucleic acid (Klein et al. (1987) *Nature* 327:70); use of pollen as vector (PCT International Patent Publication No. WO 85/01856); and use of *Agrobacterium tumefaciens* or *A. rhizogenes* carrying a T-DNA plasmid in which DNA fragments are cloned (Fraley et al. (1983) *Proc. Natl. Acad. Sci. USA* 80:4803). Any suitable method, including without limitation the specific methods explicitly identified herein, which provides for effective introduction of a nucleic acid into a cell or protoplast, may be employed in certain embodiments of the invention.

Engineered host cells can be cultured in conventional nutrient media or media modified for, for example, activating promoters or selecting transformants. In some embodiments, host plant cells may be cultured into transgenic plants. Plant regeneration from cultured protoplasts is described in, for example, Evans et al. (1983) "Protoplast Isolation and Culture," In *Handbook of Plant Cell Cultures* 1, MacMillan Publishing Co., NY, pp. 124-176; Davey (1983) "Recent Developments in the Culture and Regeneration of Plant Protoplasts," In *Protoplasts*, Birkhauser, Basel, pp. 12-29; Dale (1983) "Protoplast Culture and Plant Regeneration of Cereals and Other Recalcitrant Crops," In *Protoplasts*, supra, pp. 31-41; and Binding (1985) "Regeneration of Plants," In *Plant Protoplasts*, CRC Press, Boca Raton, Fla., pp. 21-73. Additional resources providing useful details regarding plant cell culture and regeneration include Payne et al. (1992) *Plant Cell and Tissue Culture in Liquid Systems*, John Wiley & Sons, Inc., NY; Gamborg and Phillips (eds.) (1995) *Plant Cell, Tissue and Organ Culture; Fundamental Methods*, Springer Lab Manual, Springer-Verlag (Berlin Heidelberg N.Y.); and R. R. D. Croy (Ed.) *Plant Molecular Biology* (1993) Bios Scientific Publishers, Oxford, UK (ISBN 0 12 198370 6).

Transformed plant cells that are produced using any of the above transformation techniques may be cultured to regenerate a whole plant that possesses the transformed genotype and thus the desired phenotype. Such regeneration techniques generally rely on manipulation of certain phytohormones in a tissue culture growth medium, typically relying on a biocide and/or herbicide marker that has been introduced into the cell together with the desired nucleotide sequences. Regeneration and growth processes used to produce a whole plant generally include the steps of selection of transformant cells and shoots; rooting the transformant shoots; and growth of the plantlets in soil.

Plant transformation with nucleic acids that contribute to RN resistance (e.g., that comprise markers described herein) may be used to transform species other than cotton. For example, it is contemplated that expression products from QTLs that contribute to or an RN resistance phenotype in cotton can also contribute to increased nematode resistance when transformed and expressed in other agronomically and horticulturally important plant species. Such species include dicots, for example and without limitation, of the families: Leguminosae (including pea, beans, lentil, peanut, yam bean, cowpeas, velvet beans, soybean, clover, alfalfa, lupine, vetch, lotus, sweet clover, wisteria, and sweetpea) and Compositae. Additional plants comprising nucleic acids that contribute to RN resistance in cotton (e.g., that comprise markers described herein) may be plants from among the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others.

VIII. Systems for Detecting and/or Correlating Reniform Nematode Resistance Markers Systems, including automated systems, for identifying plants that comprise at least one marker linked to an RN resistance phenotype in cotton, and/or for correlating presence of a specific linked marker allele with RN resistance, are also included in some embodiments. Exemplary systems may include probes useful for allele detection at a marker locus described herein; a detector for detecting labels on the probes; appropriate fluid handling elements and temperature controllers, for example, that mix probes and templates and/or amplify templates; and/or system instructions that correlate label detection to the presence of a particular marker locus or allele.

In particular embodiments, a system for identifying a cotton plant predicted to have RN resistance is provided. Such a system may include, for example and without limitation: a set of marker primers and/or probes configured to detect at least one allele of at least one marker linked to RN resistance (e.g., a marker set forth in Tables 2-4, and a marker linked to at least one of the foregoing); a detector that is configured to detect one or more signal outputs from the set of marker probes or primers, or amplicon thereof, thereby identifying the presence or absence of the allele; and system instructions that correlate the presence or absence of the allele with RN resistance.

A system that performs marker detection and/or correlation may include a detector that is configured to detect one or more signal outputs from the set of marker probes or primers, or amplicon thereof. The precise configuration of the detector may depend on the type of label used to detect a marker allele. Particular examples may include light detectors and/or radioactivity detectors. For example, detection of light emission or other property of a labeled probe may be indicative of the presence or absence of a marker allele interacting with the probe (e.g., via specific hybridization). The detector(s) optionally monitors one or a plurality of signals from an amplification reaction. For example, a detector may monitor optical signals which correspond to "real time" amplification assay results.

A wide variety of signal detection devices are available including, for example and without limitation, photo multiplier tubes; spectrophotometers; CCD arrays; arrays and array scanners; scanning detectors; phototubes and photodiodes; microscope stations; galvo-scanns; and microfluidic nucleic acid amplification detection appliances. In addition to the type of label used to detect a marker allele, the precise configuration of a detector may depend, in part, on the instrumentation that is most conveniently obtained for the user. Detectors that detect fluorescence, phosphorescence, radioactivity, pH, charge, absorbance, luminescence, temperature, or magnetism may be used in some examples.

The precise form of instructions provided in a system according to some embodiments may similarly vary, depending on the components of the system. For example, instructions may be present as system software in one or more integrated unit(s) of the system, or they may be present in one or more computers or computer readable media operably coupled to a detector. In some examples, system instructions include at least one reference table that includes a correlation between the presence or absence of a particular marker allele in a plant or germplasm and a predicted qualitative or quantitative level of resistance to reniform nematode infection and/or damage. Instructions may also include directions for establishing a user interface with the system; e.g., to permit a user to view results of a sample analysis and to input parameters into the system.

A system may include in particular embodiments components for storing or transmitting computer readable data representing or designating detected marker alleles, for example, in an automated (e.g., fully automated) system. For example, a computer readable media may be provided that includes cache, main, and storage memory, and/or other electronic data storage components (e.g., hard drives, floppy drives, and storage drives) for storage of computer code. Data representing alleles detected by the method of the present invention can also be electronically, optically, or magnetically transmitted in a computer data signal embodied in a transmission medium over a network, such as an intranet or internet or combinations thereof. A system may also or alternatively transmit data via wireless, infrared, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

In some embodiments, a system may be comprised of separate elements, or may alternatively be integrated into a single unit for convenient detection of markers alleles, and optionally for additionally performing marker-phenotype correlations. In particular embodiments, the system may also include a sample, for example and without limitation, genomic DNA; amplified genomic DNA; cDNA; amplified cDNA; RNA; and amplified RNA, from cotton or from a selected cotton plant tissue.

Automated systems provided in some embodiments optionally include components for sample manipulation; e.g., robotic devices. For example, an automated system may include a robotic liquid control armature for transferring solutions (e.g., plant cell extracts) from a source to a destination (e.g., from a microtiter plate to an array substrate) that may be operably linked to a digital computer (e.g., in an integrated computer system). An input device for entering data to the digital computer to control high throughput liquid transfer by the robotic liquid control armature (and, optionally, to control transfer by the armature to the solid support) may also be a feature of an automated system. Many automated robotic fluid handling systems are commercially available. For example, a variety of automated systems that utilize various ZYMATE™ systems, and typically include, robotics and fluid handling modules, are available from Caliper Technologies Corp. (Hopkinton, Mass.). Similarly, the common ORCA® robot, which is used in a variety of laboratory systems (e.g., for microtiter tray manipulation) is also commercially available from, for example, Beckman Coulter, Inc. (Fullerton, Calif.). As an alternative to conventional robotics, microfluidic systems for performing fluid handling and detection are now widely available from Caliper Technologies and Agilent technologies (Palo Alto, Calif.).

In particular embodiments, a system for molecular marker analysis may include, for example and without limitation, a digital computer comprising high-throughput liquid control software; a digital computer comprising image analysis software for analyzing data from marker labels; a digital computer comprising data interpretation software; a robotic liquid control armature for transferring solutions from a source to a destination; an input device (e.g., a computer keyboard) for entering data into the system (e.g., to control high throughput liquid transfer by the robotic liquid control armature); and an image scanner for digitizing label signals from labeled probes.

Optical images (e.g., hybridization patterns) viewed and/or recorded by a camera or other device (e.g., a photodiode and data storage device) may be further processed in any of the embodiments herein. For example and without limitation, such images may be processed by digitizing the image and/or storing and analyzing the image on a computer. A variety of commercially available peripheral equipment and software is available for digitizing, storing and analyzing a digitized video or digitized optical image, for example, using various computer and programming platforms.

Some embodiments also include kits useful for identifying plants that comprise at least one marker linked to an RN resistance phenotype in cotton, and/or for correlating presence of a specific linked marker allele with RN resistance. In some examples, such a kit may include appropriate primers or probes for detecting at least one marker linked to RN resistance and particular marker alleles; and instructions for using the primers or probes to detect the at least one marker and correlate the marker allele with a predicted qualitative or quantitative level of resistance to reniform nematode infection and/or damage. A kit may in some examples include packaging materials for packaging probes, primers, and/or instructions; and controls (e.g., control amplification reactions that include probes, primers or template nucleic acids for amplifications, and molecular size markers).

In some embodiments, a kit or system for identifying plants that comprise at least one marker linked to an RN resistance phenotype in cotton, and/or for correlating presence of a specific linked marker allele with RN resistance may include nucleic acids that detect particular SSR and/or SNP QTL markers described herein. For example, a system or kit may comprise an amplification primer pair capable of initiating DNA polymerization by a DNA polymerase on a cotton nucleic acid template to generate a cotton marker amplicon, where the marker amplicon corresponds to a cotton marker selected from those set forth in Tables 2-4 or a marker linked to at least one of the foregoing. For example, a primer pair that is specific for an SSR marker can be selected from the primer pairs set forth in Table 4, or their equivalents.

The following examples are provided to illustrate certain particular features and/or embodiments. The examples should not be construed to limit the disclosure to the particular features or embodiments exemplified.

EXAMPLES

Some embodiments are exemplified herein by the identification of a reniform nematode resistance QTL in an $F_2$ population derived from a RN-sensitive Upland varietyx Inca Cotton GB 713, the identification of tightly linked markers to this RN resistance trait, and validation and confirmation of the linked markers for marker-assisted selection of RN resistant plants in cotton. In these examples, the genotypic information derived from 181 $F_2$ individuals using an INFINIUM® assay (Illumina) was utilized to generate a linkage map with 4062 SNP and 5 SSR markers across 26 chromosomes. These $F_2$ plants were grown in soil infested with reniform nematodes to collect data correlated with resistance, as expressed by reduced nematode reproduction relative to susceptible check varieties. Corresponding $F_2$ RN resistance phenotypic information (i.e., nematode count data from the surrounding soil to the roots) was used to detect two RN resistance QTLs.

A major QTL was observed on chromosome 21 between markers DASCTP_28910_164 (22.43 cM) and DASCTP_1656_527 (23.55 cM), spanning between 0-32.62 cM with a maximum LOD score of 13.84. Based on 1000 permutations, the LOD threshold was calculated to be 4.4 at p=0.05 and 5.2 at p=0.01. This QTL explained 29.8% variation in the phenotype.

The markers were further converted into KASPar™ assays for validation and marker assisted selection of novel RN resistant plants.

Example 1: Materials and Methods

Plant Material. Inca Cotton GB713, a short day *Gossypium barbadense*, reniform nematode (RN) resistant genotype, was crossed with a RN-susceptible genotype to generate $F_1$ seeds. The $F_2$ generation was obtained by selfing $F_1$ plants the following winter.

Genomic DNA extraction and quantification. Genomic DNA from leaf tissue of individual $F_2$ plants and parents was extracted using a CTAB DNA extraction protocol. Kohel et al. (2001) *Euphytica* 121:163-72. DNA quality was assessed by gel electrophoresis, and DNA concentration was estimated using a Quant-iT™ PicoGreen® Quantification Kit (Invitrogen, Carlsbad, Calif.), according to the manufacturer's instructions. The DNA concentration was normalized to 50 ng/µL to accommodate genotyping using iSelect INFINIUM® (Illumina) assays.

Phenotypic Assay. In a greenhouse study, 214 $F_2$, 10 $BC_1F_1$, and parent seeds were germinated in 10 cm diameter clay pots containing pasteurized fine sandy loam soil, at the rate of one seedling/pot. The experimental design was a randomized complete block with five replications. On the same day of sowing, these pots were inoculated with 2,000 vermiform RN containing both juveniles and adult nematodes. All pots were watered and fertilized as necessary. Six weeks after inoculation, the RN resistance phenotypic assay on $F_2$ plants was conducted by calculating the vermiform RN. See Robbins et al. (1994) *J. Nematology* 26:659.

Genotyping with Molecular Markers. Two sets of iSelect INFINIUM® (Illumina) assays were designed with SNP markers developed from 454 sequencing of the reduced representation libraries (PstI and EcoRI) of a *G. hirsutum* and a *G. barbadense* genotype, followed by analyzing the data through the HAPSNP pipeline. A total of 5023 and 8040 assays were finally manufactured on the first and second iSelect INFINIUM® chips, respectively.

Genotyping was conducted using the DNA samples from 181 $F_2$ genotypes and parents according to the manufacturer's protocol. Scoring of the genotype clusters was completed using a custom polyploid SNP scoring method in the GENOMESTUDIO® v2011.1 software package (Illumina). Genotypic calls for polymorphic markers in the mapping population were initially scored in ternary fashion with four alleles, and later were converted into A (P06x.4433 alleles), B (GB713 alleles) and H (heterozygous alleles). Ambiguous genotype calls were converted into missing data (represented with a dash (-)) to avoid segregation artifacts. Genotype data was formatted into a locus file (.loc) for analysis with JOINMAP® 4.0. See Van Ooijen (2006) "JoinMap 4, Software for the calculation of genetic linkage maps in experimental populations," Kyazma B.V., Wageningen, NL.

Quantitative Trait Loci (QTL) mapping. MAPQTL® 6.0 (Van Ooijen (2009) MapQTL® 6, Software for the mapping of quantitative trait loci in experimental populations of diploid species," Kyazma B. V., Wageningen, NL) was used to map the QTLs. MapQTL® 6.0 requires three input files, including a locus genotype file, a map file, and a quantitative data file. The locus genotype file (.loc file) contained the genotype codes for all loci of the segregating population. The map file was generated from JOINMAP®, and it contained the estimated map positions of all loci. The quantitative data file (.qua file) contained the nematode count and resistance call from the mapping population. In the .qua file, resistance call information was converted from character datatype to numerical score as in: HR=1; R=2, MR=3, S=4. Analysis using an interval between two markers was performed, and the likelihood that a QTL was within an interval was calculated as a logarithm of odds (LOD) score. When a LOD score exceeded the predefined significance threshold on a linkage group, a segregating QTL was detected, and the position with the largest LOD on the linkage group was the estimated position of the QTL on the map.

Example 2: Phenotypic Reniform Nematode Resistance Assay

Despite the photoperiodic nature of the Inca Cotton GB 713, a *G. barbadense* genotype, a cross-pollination was produced with a *G. hirsutum* genotype (Upland cotton) that has a high level of resistance to the root-knot nematode (*Meloidogyne incognita*). An $F_2$ mapping population was produced through traditional hybridization practices. A phenotypic screen for reniform resistance was conducted in this population by collecting the nematode count data from the soil 6 weeks after inoculating individuals with ~2,000 adult and juvenile nematodes/pot, which in turn represents the extent of RN reproduction. The phenotypic data contained the number of nematodes in each pot, along with a resistance classification as highly resistant (HR<250 RN), resistant (251<R<1500 RN), moderately resistant (1501<MR<9200 RN) and susceptible (S>9200 RN).

Figure 2:
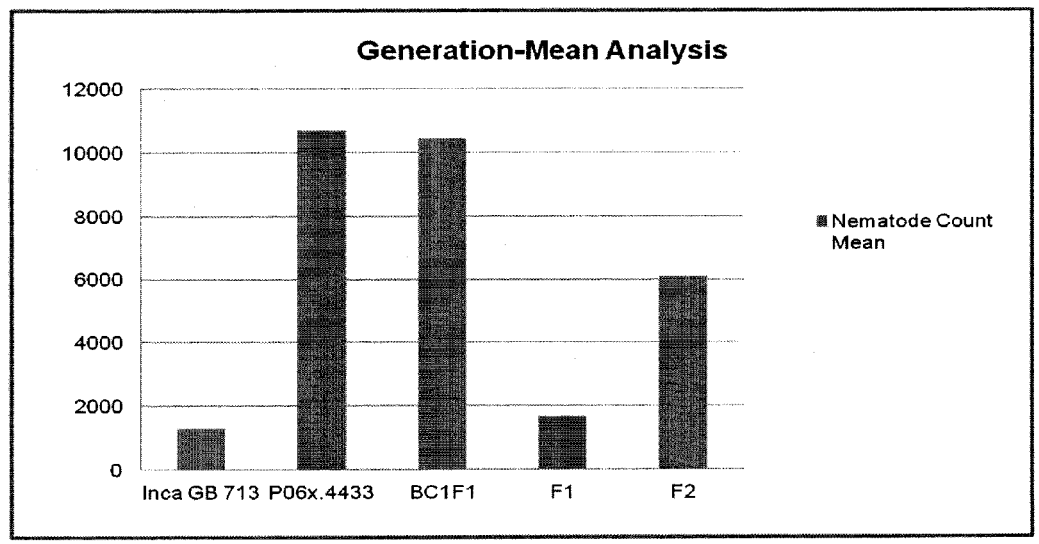
FIG. 2 includes a generation-mean analysis based on RN count data in the phenotypic screen.

The number of nematodes ranged from 138 to 24,806 during the phenotypic screen. The values were converted into $\log_{10}(X+1)$ to normalize the variability in the phenotypic assay. The frequency distribution of the $\log_{10}(X+1)$ values for each of the generations in this study and generation-mean analysis based on nematode count is represented in FIGS. 1-2. Based on generation-mean analysis, there were significant differences in the nematode count data between the $F_1$, $F_2$, and $BC_1F_1$ generations. In the $BC_1F_1$ generation (backcrossed to susceptible parent), the mean $\log_{10}(X+1)$ value was skewed towards the susceptible parent. This suggests that the inheritance of this trait is through partial dominance.

Two cotton custom-built INFINIUM® assays with 13063 SNP markers and 6 simple sequence repeat (SSR) markers were initially evaluated for polymorphism detection between the parental lines, and were also used to generate genotyping information. A total of 4091 markers including 4086 SNPs and 5 SSRs were polymorphic between the parents, and allele calls were recorded in ternary fashion for the mapping population. The majority of the markers were in concordance with the typical $F_2$ segregation ratio of 1:2:1 for the co-dominant and dominant markers.

The genetic linkage map was constructed with 4062 SNP and 5 SSR markers across all 26 chromosomes, spanning 4755.2 cM in total linkage distance. The average SNP marker density was approximately 156 markers per chromosome, and the average distance between the adjacent markers was 1 marker per every 1.17 cM. Table 1.

TABLE 1

SNP marker coverage and linkage distance information from P06x.4433 × GB713 genetic map.

| Chromosome | # Markers | cM | Average Marker Density/Chromosome |
| --- | --- | --- | --- |
| 1 | 93 | 170.003 | 1.827989 |
| 2 | 135 | 155.215 | 1.149741 |
| 3 | 194 | 175.523 | 0.904758 |
| 4 | 131 | 135.209 | 1.03213 |
| 5 | 215 | 277.216 | 1.289377 |
| 6 | 164 | 183.425 | 1.118445 |
| 7 | 157 | 186.453 | 1.187599 |

TABLE 1-continued

SNP marker coverage and linkage distance information from P06x.4433 × GB713 genetic map.

| Chromosome | # Markers | cM | Average Marker Density/Chromosome |
|---|---|---|---|
| 8 | 156 | 168.155 | 1.077917 |
| 9 | 166 | 213.766 | 1.287747 |
| 10 | 203 | 241.071 | 1.187542 |
| 11 | 174 | 210.237 | 1.208259 |
| 12 | 199 | 197.157 | 0.990739 |
| 13 | 186 | 237.979 | 1.279457 |
| 14 | 162 | 168.496 | 1.040099 |
| 15 | 134 | 142.294 | 1.061896 |
| 16 | 146 | 171.051 | 1.171582 |
| 17 | 133 | 148.258 | 1.114722 |
| 18 | 155 | 155.718 | 1.004632 |
| 19 | 143 | 211.273 | 1.477434 |
| 20 | 145 | 190.851 | 1.316214 |
| 21 | 182 | 194.822 | 1.070451 |
| 22 | 131 | 168.822 | 1.288718 |
| 23 | 124 | 193.05 | 1.556855 |
| 24 | 137 | 138.835 | 1.013394 |
| 25 | 159 | 153.686 | 0.966579 |
| 26 | 143 | 166.651 | 1.165392 |
| Total Linkage Distance | 4067 | 4755.216 | 1.16922 |

Example 3: QTL Mapping

Based on the interval mapping results, the RN resistance was mapped to a major QTL on chromosome 21.

Figure 3:
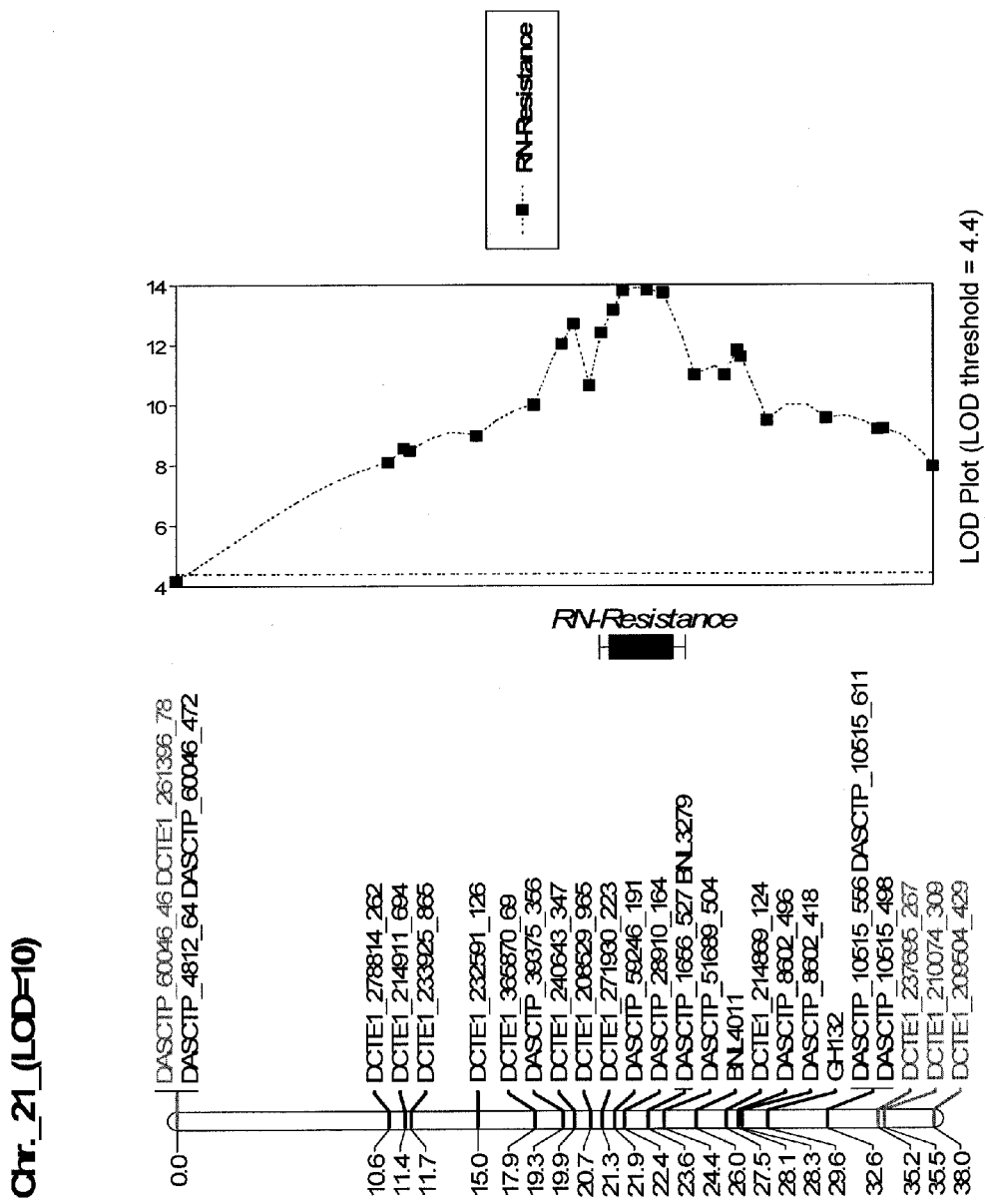
FIG. 3 includes a map of the QTL region on chromosome 21, showing the peak LOD location and linked markers in dark text.
Figure 4:
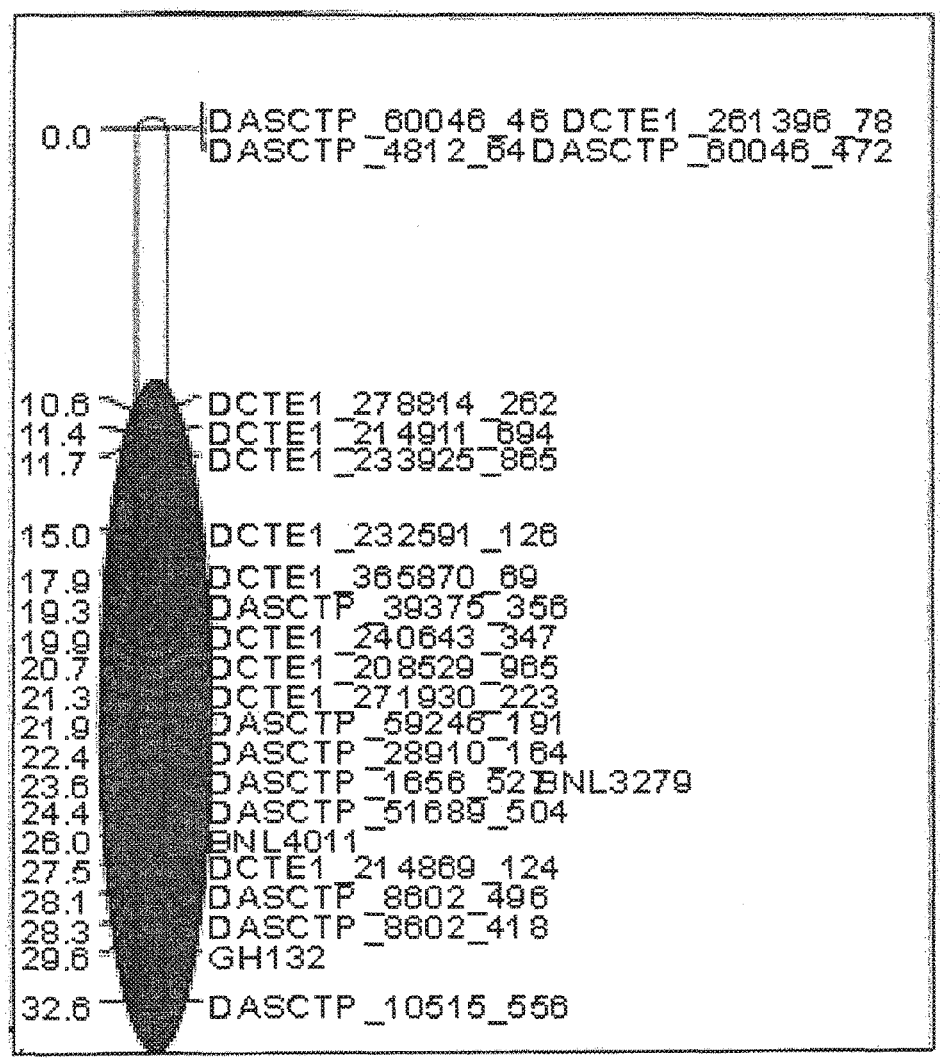
FIG. 4 includes a graphical representation of marker-trait association in the QTL region with LOD and % Explanation of RN resistance trait.

Chromosome 21 had a total of 182 markers spanning 194.8 cM, with average marker coverage every 1.07 cM. The major QTL region was concentrated at the distal end of the chromosome, between 0 and 32.62 cM, with a maximum LOD score of 13.93 observed between DASCTP_28910_164 and DASCTP_1656_527. This major QTL explained 29.8% of the variation in the resistance phenotype. Though two additional QTL LOD peaks were detected on chromosome 21: (i) a QTL LOD peak on chromosome 21 between DASCTP_39375_356 (19.33cM) and DCTE1_208529_965 (20.74cM); and (ii) a QTL LOD peak region on chromosome 21 between DCTE1_214869_124 (27.49cM) and DASCTP_8602_418 (28.33cM), they were considered as parts of one major QTL region. The details of the QTL region on chromosome 21 is represented in Tables 2-4 and FIGS. 3-4.

TABLE 2

Markers, LOD score, and % explanation in the QTL regions associated with RN resistance on chromosome 21. Italicized QTL loci explain maximum RN resistance variation.

| Chromosome | cM | Marker Name | LOD | % Explanation |
|---|---|---|---|---|
| Chr 21 | 0.00 | DASCTP_4812_64 | 4.18 | 10.1 |
| Chr 21 | 0.00 | DASCTP_60046_46 | 4.18 | 10.1 |
| Chr 21 | 0.00 | DASCTP_60046_472 | 4.18 | 10.1 |
| Chr 21 | 0.00 | DCTE1_261396_78 | 4.18 | 10.1 |
| Chr 21 | 1.00 | | 4.60 | 11.1 |
| Chr 21 | 2.00 | | 5.04 | 12.0 |
| Chr 21 | 3.00 | | 5.48 | 13.0 |
| Chr 21 | 4.00 | | 5.92 | 14.0 |
| Chr 21 | 5.00 | | 6.35 | 14.9 |
| Chr 21 | 6.00 | | 6.75 | 15.8 |
| Chr 21 | 7.00 | | 7.13 | 16.6 |
| Chr 21 | 8.00 | | 7.46 | 17.3 |
| Chr 21 | 9.00 | | 7.74 | 17.9 |
| Chr 21 | 10.00 | | 7.98 | 18.4 |
| Chr 21 | 10.56 | DCTE1_278814_262 | 8.09 | 18.6 |
| Chr 21 | 11.42 | DCTE1_214911_694 | 8.56 | 19.6 |
| Chr 21 | 11.69 | DCTE1_233925_865 | 8.49 | 19.4 |
| Chr 21 | 12.69 | | 8.88 | 20.2 |
| Chr 21 | 13.69 | | 9.09 | 20.6 |
| Chr 21 | 14.69 | | 9.04 | 20.5 |
| Chr 21 | 14.97 | DCTE1_232591_126 | 8.97 | 20.4 |
| Chr 21 | 15.97 | | 9.48 | 21.4 |
| Chr 21 | 16.97 | | 9.84 | 22.1 |
| Chr 21 | 17.89 | DCTE1_365870_69 | 10.01 | 22.5 |
| Chr 21 | 18.89 | | 11.65 | 25.6 |
| Chr 21 | 19.33 | DASCTP_39375_356 | 12.04 | 26.4 |
| *Chr 21* | *19.90* | *DCTE1_240643_347* | *12.71* | *27.6* |
| Chr 21 | 20.75 | DCTE1_208529_965 | 10.66 | 23.8 |
| Chr 21 | 21.31 | DCTE1_271930_223 | 12.01 | 27 |
| Chr 21 | 21.87 | DASCTP_59246_191 | 13.17 | 28.5 |
| *Chr 21* | *22.43* | *DASCTP_28910_164* | *13.82* | *29.7* |
| *Chr 21* | *23.43* | | *13.93* | *29.8* |
| *Chr 21* | *23.55* | *BNL3279* | *13.84* | *29.7* |
| *Chr 21* | *23.55* | *DASCTP_1656_527* | *13.84* | *29.7* |
| Chr 21 | 24.39 | DASCTP_51689_504 | 13.75 | 29.5 |
| Chr 21 | 25.39 | | 12.23 | 26.7 |
| Chr 21 | 25.96 | BNL4011 | 11.01 | 24.4 |
| Chr 21 | 26.96 | | 11.29 | 25.0 |
| Chr 21 | 27.50 | DCTE1_214869_124 | 11.01 | 24.4 |
| *Chr 21* | *28.05* | *DASCTP_8602_496* | *11.82* | *26.0* |
| Chr 21 | 28.33 | DASCTP_8602_418 | 11.61 | 25.6 |
| Chr 21 | 29.33 | | 10.06 | 22.6 |
| Chr 21 | 29.63 | GH132 | 9.49 | 21.4 |
| Chr 21 | 30.63 | | 10.00 | 22.5 |
| Chr 21 | 31.63 | | 10.01 | 22.5 |
| Chr 21 | 32.62 | DASCTP_10515_556 | 9.56 | 21.6 |

TABLE 3

SNP markers linked to the major QTL on chromosome 21 with their resistant and susceptible genotypes.

| Marker | SEQ ID NO. | SNP | IncaGB713 (Resistant) Allele | Upland (Susceptible) Allele |
|---|---|---|---|---|
| DASCTP_4812_64 | SEQ ID NO: 1 | [A/G] | AA | GG |
| DASCTP_60046_472 | SEQ ID NO: 2 | [A/G] | AA | GG |
| DCTE1_261396_78 | SEQ ID NO: 3 | [T/C] | TT | CC |
| DASCTP_60046_46 | SEQ ID NO: 4 | [T/G] | TT | GG |
| DCTE1_278814_262 | SEQ ID NO: 5 | [T/C] | TT | CC |
| DCTE1_214911_694 | SEQ ID NO: 6 | [T/C] | CC | TT |
| DCTE1_233925_865 | SEQ ID NO: 7 | [A/G] | GG | AA |
| DCTE1_232591_126 | SEQ ID NO: 8 | [A/C] | AA | CC |
| DCTE1_365870_69 | SEQ ID NO: 9 | [A/G] | AA | GG |
| DASCTP_39375_356 | SEQ ID NO: 10 | [A/G] | AA | GG |
| DCTE1_240643_347 | SEQ ID NO: 11 | [A/G] | AA | GG |
| DCTE1_208529_965 | SEQ ID NO: 12 | [T/C] | CC | TT |
| DCTE1_271930_223 | SEQ ID NO: 13 | [T/G] | GG | TT |
| DASCTP_59246_191 | SEQ ID NO: 14 | [A/G] | GG | AA |

TABLE 3-continued

SNP markers linked to the major QTL on chromosome 21 with their resistant and susceptible genotypes.

| Marker | SEQ ID NO. | SNP | IncaGB713 (Resistant) Allele | Upland (Susceptible) Allele |
|---|---|---|---|---|
| DASCTP_28910_164 | SEQ ID NO: 15 | [T/C] | CC | TT |
| DASCTP_1656_527 | SEQ ID NO: 16 | [T/G] | GG | TT |
| DASCTP_51689_504 | SEQ ID NO: 17 | [A/G] | AA | GG |
| DCTE1_214869_124 | SEQ ID NO: 18 | [T/G] | GG | TT |
| DASCTP_8602_496 | SEQ ID NO: 19 | [T/C] | CC | TT |
| DASCTP_8602_418 | SEQ ID NO: 20 | [A/C] | AA | CC |
| DASCTP_10515_556 | SEQ ID NO: 21 | [A/G] | GG | AA |

TABLE 4

SSR markers linked to the QTLs on chromosome 21.

| Marker | Chromosome | Primer | SEQ ID NO. |
|---|---|---|---|
| BNL3279 | 21 | Forward | SEQ ID NO: 22 |
| BNL3279 | 21 | Reverse | SEQ ID NO: 23 |
| BNL4011 | 21 | Forward | SEQ ID NO: 24 |
| BNL4011 | 21 | Reverse | SEQ ID NO: 25 |
| GH132 | 21 | Forward | SEQ ID NO: 26 |
| GH132 | 21 | Reverse | SEQ ID NO: 27 |

Example 4: SNP Detection Pipeline for Polyploid Species

Cotton was used as a model species to test and validate a haplotype based SNP detection pipeline: HAPSNP pipeline. Using genome complexity reduction approach, two cotton varieties, one of species G. hirsutum and one of species G. barbadense, were sequenced using 454 sequencing technology. Sequence information thus generated was processed through HAPSNP pipeline comprising (1) Assembly/mapping; (2) SNP calling; (3) SNP filtration; (4) Haplotype calling; and (5) SNP sequence formatting modules. The diagrammatic representation of the pipeline was summarized as a flowchat in FIG. 5.

Figure 5:
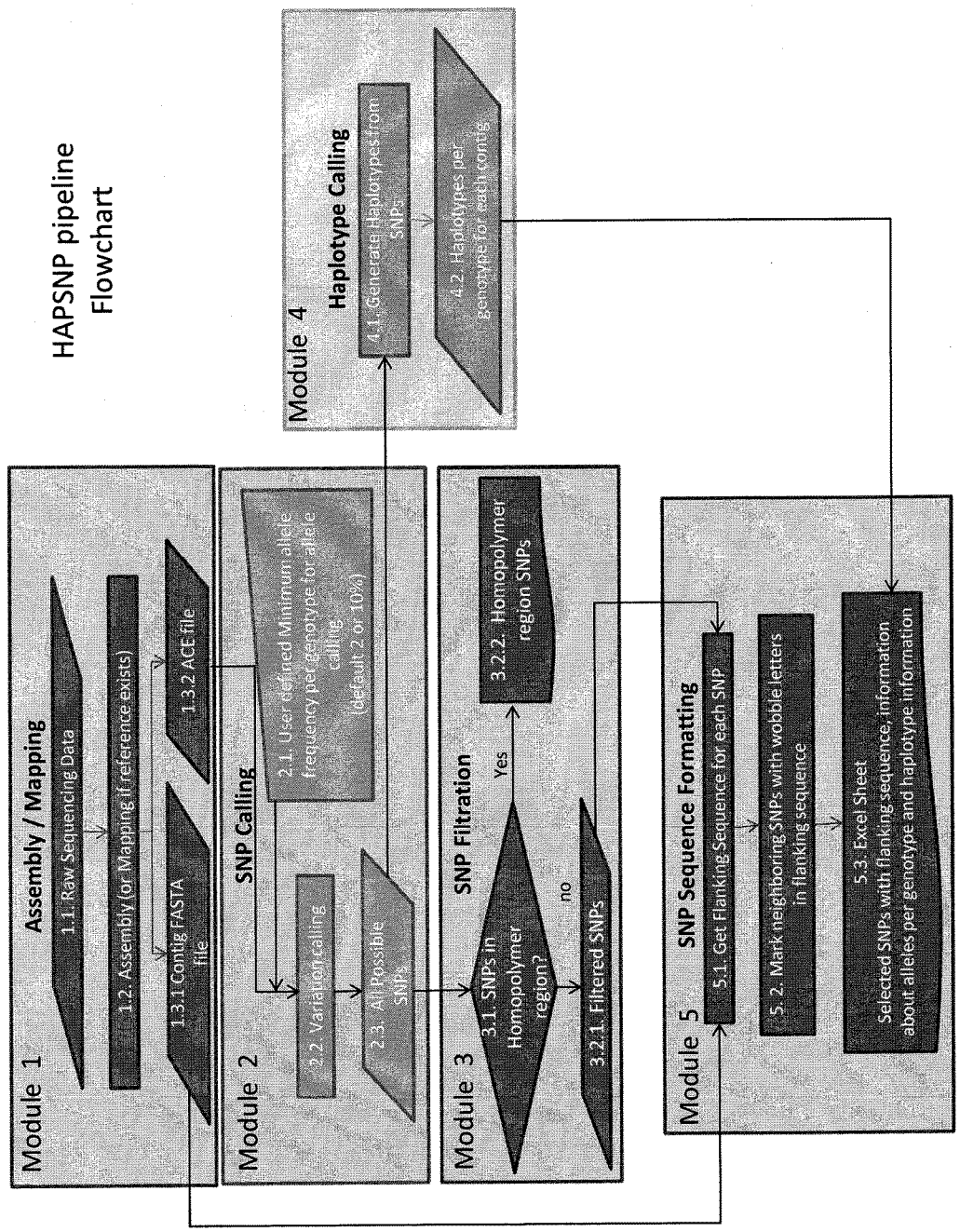
FIG. 5 includes a flow chart depiction of an SNP detection pipeline.

Sequencing data from cotton can be imported directly into the assembly/mapping module of the HAPSNP pipeline provided as shown in FIG. 5. After assembly/mapping (for example, see Module 1 of FIG. 5), the output .ace (or ACE) file can be input into the SNP calling module (for example, see Module 2 of FIG. 5). The SNP calling module determines all possible SNPs based on sequence comparison among all input sequences and optionally a reference sequence is considered for sequence comparison. Contig sequences and identifiers can be included in all SNPs as output after SNP calling as shown in FIG. 5. These SNPs/contigs are then subject to SNP filtration (for example, see Module 3 of FIG. 5). The SNP filtration module can also determine whether SNPs are in a homopolymer region. After SNP filtration, false positive SNPs are removed and input into a SNP sequence formatting module as shown in FIG. 5.

Separately, all possible SNPs are subject to the haplotype calling module (for example, see Module 4 of FIG. 5). The haplotype calling module can optionally include a haplotype filtration unit which is independent from the SNP filtration module. The haplotype information can be input into the SNP sequence formatting module to be considered for association with genotypes after combination with filtered SNPs.

Finally, the SNP sequence formatting module (for example, see Module 5 of FIG. 5) complies filtered SNP with flanking sequences together with haplotype information (optionally filtered) to determine contigs containing high quality SNP markers for testing purposes.

Candidate or true SNPs are bi-allelic, with each genotype supporting one allele in homologous condition, with a minimum of 2 sequences. Hemi-SNPs are tri-allelic, where one genotype in the haplotype cluster is bi-allelic or heterozygous, and the other genotype is mono-allelic or in homozygous condition. Paralogous SNPs are bi-allelic or heterozygous within a genotype. True and HemiSNPs can be used for genetic mapping purposes. Paralogous SNPs are less useful in genetic mapping. Based on the position of the candidate SNP loci, flanking sequence information was fetched 100 bp upstream and downstream of the SNP and formatted with [allele1/allele2] info at the SNP locus for the assay design.

From 454 sequencing of the reduced representation libraries (PstI and EcoRI) of G. hirsutum and G. barbadense genotypes, followed by analyzing the data through the HAPSNP pipeline, two sets of iSelect INFINIUM® (Illumina) assays were designed with the resulting SNP markers. A total of 5023 and 8040 assays were finally manufactured on the first and second iSelect INFINIUM® chips, respectively. These chips were used for the genotyping purpose in the current study.

This HAPSNP pipeline helps to identify high quality SNPs with high validation rate in polyploid species such as cotton. Discrimination of paralogous and homeologous SNPs from homologous SNPs is easier and more accurate than conventional methods. This pipeline will provide superior selection of candidate in silico SNPs for validation in polyploid species while reducing the occurrence of false positive SNPs.

Example 5: Validation and Application of SNP Markers Associated with Reniform Nematode Resistance for Molecular Breeding in Cotton A back cross population (BC1F1) was generated by crossing an F1 plant derived from initial cross of the RN-susceptible *G. hirsutum* variety×Inca Cotton GB713 with the RN-susceptible variety to introgress the RN resistance from GB713 into Upland cotton cultivars. This population is used to validate Marker-RN resistance trait association.

A phenotypic screen for reniform resistance was conducted in this population by collecting the nematode count data from the soil 6 weeks after inoculating individuals with ~2,000 adult and juvenile nematodes/pot, which in turn represents the extent of RN reproduction. The phenotypic data contained the number of nematodes in each pot pot.

Six SNP markers vs. DASCTP_39375_356 (19.33 cM), DASCTP_59246_191 (21.87 cM), DASCTP_1656_527 (23.55 cM), DASCTP_51689_504 (24.39 cM), DASCTP_8602_496 (28.05 cM), DASCTP_8602_418 (28.33 cM) from Chromosome 21 major QTL region were used validate marker-RN resistance trait association.

TABLE 5

SNP markers used to test Marker-Trait Association

| Chromosome | Marker | Position (cM) |
|---|---|---|
| 21 | DASCTP_39375_356 | 19.33 |
| 21 | DASCTP_59246_191 | 21.87 |
| 21 | DASCTP_1656_527 | 23.55 |
| 21 | DASCTP_51689_504 | 24.39 |
| 21 | DASCTP_8602_496 | 28.05 |
| 21 | DASCTP_8602_418 | 28.33 |

SNP markers were converted into KASPar assays and were used to genotype the BC1F1 population. The genotypic information combined with phenotypic data was used to conduct "Single Marker Analysis" using "Windows QTL Cartographer" program.

Single Marker Analysis fits the data to the simple linear regression model $y = b_0 + b_1 x + e$ The results below give the estimates for $b_0$, $b_1$ and the F statistic for each marker. This analysis is frequently used to verify if a marker is linked to a QTL. This is tested by determining if $b_1$ is significantly different from zero. The F statistic compares the hypothesis H0: $b_1 = 0$ to an alternative H1: $b_1$ not 0. The pr(F) is a measure of how much support there is for H0. A smaller pr(F) indicates less support for H0 and thus more support for H1. Significance at the 5%, 1%, 0.1% and 0.01% levels are indicated by *, , * and ****, respectively. Note that Likelihood ratio test statistic compares two nested hypotheses and is two times the negative natural log of the ratio of the likelihoods. For example, assume that hypothesis H0 is nested within H1 and that they have likelihoods L0 and L1, respectively. Then, the "Likelihood Ratio Test Statistic" is $-2 \ln(L0/L1)$. $-t1$ is the number of trait being analyzed.

TABLE 6

Single Marker Analysis for Marker-RN resistance trait association

| Chromosome | Marker | Position | b0 | b1 | $-2\ln(L0/L1)$ | $F(1, n-2)$ | pr(F) |
|---|---|---|---|---|---|---|---|
| 21 | DASCTP_39375_356 | 19.33 | 2700.714 | −1526.92 | 5.127 | 5.177 | 0.027* |
| 21 | DASCTP_59246_191 | 21.87 | 2643.992 | −1058.82 | 2.486 | 2.452 | 0.123 |
| 21 | DASCTP_1656_527 | 23.55 | 2676.744 | −1342.34 | 4.074 | 4.075 | 0.048* |
| 21 | DASCTP_51689_504 | 24.39 | 2700.714 | −1439.23 | 4.531 | 4.551 | 0.037* |
| 21 | DASCTP_8602_496 | 28.05 | 2700.714 | −1439.23 | 4.531 | 4.551 | 0.037* |
| 21 | DASCTP_8602_418 | 28.33 | 2728.601 | −1552.96 | 5.094 | 5.143 | 0.027* |

Markers DASCTP_39375_356 (19.33 cM), DASCTP_1656_527 (23.55 cM), DASCTP_51689_504 (24.39 cM), DASCTP_8602_496 (28.05 cM), DASCTP_8602_418 (28.33 cM) were found to be significant at 5% level and are indicated by * in pr(F) column. This confirms RN resistance trait association with SNP markers from major QTL region in chromosome 21 and to select RN resistant plants through MAS.

As these markers were confirmed for their association with RN resistance through statistical test, we evaluated the genotype information for advanced breeding generations from the two crosses to predict the phenotype and further advance the lines with resistant loci in the breeding program.

Using RN resistance marker information, we were able to assist the breeding of RN resistant cotton by providing selections based upon the resistant marker loci for advancement. Marker information between these candidate loci from the consensus map may be utilized to develop new SNP markers associated with the RN resistance.

While the foregoing embodiments have been described in detail for purposes of clarity and understanding, it will be clear to one skilled in the art from a reading of this disclosure that various changes in form and detail can be made without departing from the true scope of the invention. For example, all the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What may be claimed is:

1. A method for producing a cotton plant comprising reniform nematode resistance, wherein the method comprises:
   crossing a parent *Gossypium* plant having a single nucleotide polymorphism (SNP) marker DASCTP_1656_527 with a parent *G. hirsutum* cotton plant to produce F1 progeny plants, wherein the SNP marker DASCTP_1656_527 is positively correlated with reniform nematode (RN) resistance;
   selecting one or more F1 progeny plants that have the SNP marker DASCTP_1656_527 to produce selected F1 progeny plants;
   crossing the selected F1 progeny plants with a second cotton plant to produce F2 progeny plants.

2. The method according to claim 1, wherein the parent *G. hirsutum* cotton plant is sensitive to RN infection as compared to the parent *Gossypium* plant having the SNP marker DASCTP_1656_527, and wherein the selected F1 progeny plant comprises increased RN resistance as compared to the parent *G. hirsutum* cotton plant.

3. The method according to claim 1, wherein the parent *G. hirsutum* cotton plant is a plant from an elite cotton variety.

4. The method according to claim 1, wherein the parent *G. hirsutum* cotton plant is Upland cotton.

5. The method according to claim 1, wherein the parent *G. hirsutum* cotton plant comprises root knot nematode (RKN) resistance.

6. The method according to claim 5, wherein the selected F1 progeny plant comprises increased RN resistance as compared to a selected F1 progeny plant that does not comprise RKN resistance.

7. The method according to claim 1, wherein the method further comprises selecting one or more F2 progeny plants that have the SNP marker allele to produce selected F2 progeny plants.

8. The method according to claim 7, wherein the method further comprises repeating the crossing and selection step three or more times, to produce selected fourth or higher progeny plants that have the SNP marker allele.

9. The method according to claim 1, wherein the second cotton plant is a plant from an elite cotton variety.

* * * * *

SEQUENCE LISTING

<160> NUMBER OF SEQ ID NOS: 27

<210> SEQ ID NO 1
<211> LENGTH: 214
<212> TYPE: DNA
<213> ORGANISM: Gossypium sp.
<220> FEATURE:
<221> NAME/KEY: variation
<222> LOCATION: (64)..(64)
<223> OTHER INFORMATION: SNP: marker DASCTP_4812_64
<220> FEATURE:
<221> NAME/KEY: misc_feature
<222> LOCATION: (153)..(153)
<223> OTHER INFORMATION: n is a, t, c or g
<220> FEATURE:
<221> NAME/KEY: misc_feature
<222> LOCATION: (203)..(203)
<223> OTHER INFORMATION: n is a, t, c or g

<400> SEQUENCE: 1

```
ggtataatat ggcatcgaat gcaaataagt tttcctttgt caacaccgga agctcatctg      60
cacrtgatag taagatagaa ctgacaagaa aaggatcagt atgcgatgtt caatctcctt     120
tggttaatga cctttccaat cagtactcaa atngttggta gcaataacat caatatggcc    180
tctacaactg ataatgcttt tgnccaagcc agct                                 214
```

<210> SEQ ID NO 2
<211> LENGTH: 301
<212> TYPE: DNA
<213> ORGANISM: Gossypium sp.
<220> FEATURE:
<221> NAME/KEY: misc_feature
<222> LOCATION: (11)..(11)
<223> OTHER INFORMATION: n is a, t, c or g
<220> FEATURE:
<221> NAME/KEY: misc_feature
<222> LOCATION: (103)..(103)
<223> OTHER INFORMATION: n is a, t, c or g
<220> FEATURE:
<221> NAME/KEY: misc_feature
<222> LOCATION: (130)..(130)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_60046_472
<220> FEATURE:
<221> NAME/KEY: misc_feature
<222> LOCATION: (216)..(216)
<223> OTHER INFORMATION: n is a, t, c or g
<220> FEATURE:
<221> NAME/KEY: misc_feature
<222> LOCATION: (230)..(230)
<223> OTHER INFORMATION: n is a, t, c or g
<220> FEATURE:
<221> NAME/KEY: misc_feature
<222> LOCATION: (288)..(288)
<223> OTHER INFORMATION: n is a, t, c or g

<400> SEQUENCE: 2

```
atcgatgctt nccggaaaaa ggtatccaat gtcgacctgt tagcataatt tctgagattc      60
agagtaaatt cttctcaaca ttttgccttt cttttttccag gtnccgatat caaagtagga    120
aaaggttagn cacaacaacg acctcgtatc ygagggcaat tcgtgtgaca aacggtgaac    180
accaatgacc cctcatctga aggcaattca tccgancaaa tagcaaagan ggaaaacact    240
agaagagtcc agctgataag gtaacaagat ttgatccact cctctganta aaataccttg    300
t                                                                     301
```

```
<210> SEQ ID NO 3
<211> LENGTH: 349
<212> TYPE: DNA
<213> ORGANISM: Gossypium sp.
<220> FEATURE:
<221> NAME/KEY: variation
<222> LOCATION: (78)..(78)
<223> OTHER INFORMATION: SNP: marker DCTE1_261396_78

<400> SEQUENCE: 3
gaatataatt ttatatataa aattaacact acattttggc gaaatcctag gaggaagcaa      60
agaagttcat gacctctycc agaaaaattc agtaccacat tgggggtat gcgagccgcg     120 ttaggtttga agttcgggat gcaagtgtca caacgcaata acttaacggg ggtgtggcag    180
caacggtttt atttgatgtt ggtggacatt ctgctatcaa tgaaatttta tatcgcaaag    240
atgttagagt tttgtacttc tcattgtcgt catctttaaa atacgaaaaa gggatatggt    300
ataatatata tacacagtaa gagttctttt aggcatgaat ttaattatt                349

<210> SEQ ID NO 4
<211> LENGTH: 196
<212> TYPE: DNA
<213> ORGANISM: Gossypium sp.
<220> FEATURE:
<221> NAME/KEY: variation
<222> LOCATION: (46)..(46)
<223> OTHER INFORMATION: SNP: marker DASCTP_60046_46

<400> SEQUENCE: 4
gacgctcccc attgtgggtc atccaatgtg ttgggtgggc ctgttmctgt tgaaggaaat     60
gctggcaact acagtgtcaa tggaagtaac tcgggtagta accacgcaag caatgggcca   120
catggaagta gcaccctagc cgatactgta gggacaaaca tagaaagcga taatggaata   180
gctgggaaaa gtggaa                                                    196

<210> SEQ ID NO 5
<211> LENGTH: 389
<212> TYPE: DNA
<213> ORGANISM: Gossypium sp.
<220> FEATURE:
<221> NAME/KEY: variation
<222> LOCATION: (262)..(262)
<223> OTHER INFORMATION: SNP: marker DCTE1_278814_262

<400> SEQUENCE: 5
aactacatag gccctggctg gtgctcttgc ctctgactgt tgtgtaacta tgttactact      60
tctaagaaca ccttcacctc tggataccga actacctcta cctaaccctc tgcctctagt    120
agtaggcatt gatatctgag atgatgtagg tatagcacat tcactttttg gacaatctca    180
gatgaaatga tctgtggacc cgcattgaaa acaccgtcga gttatcttta aacattcgcc    240
aaagtgcttc tttccatagt gytcacagtc ggggatatca atatttcgta aaggtccctt    300
tacactacct gtagaaacag tagtctgttt accccgattt ttatcaccca gatccgatct    360
gaaacttgac ctccaattgc ctctgaatt                                       389

<210> SEQ ID NO 6
<211> LENGTH: 843
<212> TYPE: DNA
<213> ORGANISM: Gossypium sp.
<220> FEATURE:
<221> NAME/KEY: variation
<222> LOCATION: (501)..(501)
<223> OTHER INFORMATION: SNP: marker DCTE1_214911_694
```

-continued

<400> SEQUENCE: 6

```
gtatgtatag ttttagtaaa taatactaag ggtttgaact tgattttgat tttctgggtt      60
tcttgattgg attttgtttg attgttttta caagaattgg tgccacatgt tagagagatt     120
ggaagcttgt attgcttgta atgggagatt gttgatctcc tttgaatgac tgagttgaat     180
tgttcaataa aatcaagatt gacgagttat gttgtgtcaa cttttgaatt aatttgtctt     240
gtcaagacag aaccatcaat gctcatgcat aaaatccaat ggttctaggc tgatgtttct     300
agcttgtact cagcgttgtt tgtttcctta gagtctaaga aaaactgata agcaaagaga     360
atattagata tgcaatggtt gataccgtgc atgaaaagag aagatatttt gtgctgcaac     420
atgtaaccaa aggtatctcc ttagcaacct tcattatttt ggttccatca actcggtatc     480
aggtgcgctt cccaacaatc ycagcagggt gcactctatc ttcaagcagg gcaccatgga     540
caccagtgag tgctcgggtg cgaggaggcc gaaatgcaga tcctttttg ggtggcctca      600
atatcctcct gttggcaagc actacaacag ccggcaaaag catgcatgaa ccaatacaac     660
ataaattaag tctaccagcc aagtaactcc tggctgcagc aatgagaggt ttggtttata     720
aaaaggcaac gccttcgcca cgacgagagg tttggttgag gaaattagga tgaactcgta     780
ttgaaagaag caatggtggt gtggttgcct ttccaaagcc gaaatggttt cttatacaga     840
gct                                                                  843
```

<210> SEQ ID NO 7
<211> LENGTH: 531
<212> TYPE: DNA
<213> ORGANISM: Gossypium sp.
<220> FEATURE:
<221> NAME/KEY: variation
<222> LOCATION: (501)..(501)
<223> OTHER INFORMATION: SNP: marker DCTE1_233925_865

<400> SEQUENCE: 7

```
ttcattttca tttcatttt ttttataaaa attcgattca aaaaattagt ttcgacaacc       60
tattaatcca atttagacta ataactattg taagttctct ttaaacaaaa aaattcaata     120
aattaataaa taacaaaaat aattaagtaa aagtgaaaaa atggcaaaaa agtcattcaa     180
tctctcgctt tttgtctttc aattagaccg ttgcagagtc tcaaatcact tttttaatat     240
caaacttaaa aacacaatgt attccagagt gaaccttcaa gtttcattta aaaatgggag     300
agacaagtga acctctgcgg caaacccctg aaccaaactc tgcttctttg gagtctctgt     360
tccatgttct cgaccctatt tctctcattc ataattcaag ccccggtaac ccaattcctt     420
taaggcttac aacagagagt tctataatgg aaaggggtcc cagatatgga gcttatgcag     480
agctaagaga aacaaagctg rgaatgaaga gtgggatgat gcaacaagaa a             531
```

<210> SEQ ID NO 8
<211> LENGTH: 567
<212> TYPE: DNA
<213> ORGANISM: Gossypium sp.
<220> FEATURE:
<221> NAME/KEY: variation
<222> LOCATION: (126)..(126)
<223> OTHER INFORMATION: SNP: marker DCTE1_232591_126
<220> FEATURE:
<221> NAME/KEY: misc_feature
<222> LOCATION: (524)..(524)
<223> OTHER INFORMATION: n is a, t, c or g

<400> SEQUENCE: 8

```
aaaaaagttc aggccccaat ttgcgaacaa ttgccaagtt caatgactaa cttagacaaa      60
```

```
aaaaaatttc aagcaccaat gtgggaacaa ttattaagtt caggccccaa atagtgcatt      120
aaccamaaaa aaaggtgaac caaaatagat atgcagaaag ccaaacctat atgtgtgcat      180
gaatgcactt gtgaacttgg acatgtgtct tatggtatat ttccctaata aggctaaagg      240
tagtttcatt ttcatggatg ggtaagagac ctctagatttt gtaaatcact gaagggaaag     300
aaattaccca tgagaatatg tcatcttctg ctgagcttga cgcaggactc atcgggctct      360
ggctgtgagc tgtccatcgt tgttctatag gagcaggagc aggtaactca ttcgtctcaa      420
tgagtttctt tagctcttca atgtactcaa ggtccttcat actaggcttg aaagagttc       480 cagcaggaaa acaggtttct gatacccatt gttggccccc caanaatcaa agcccaagat      540
atcatcactc catccaactc gatatcc                                         567
```

```
<210> SEQ ID NO 9
<211> LENGTH: 374
<212> TYPE: DNA
<213> ORGANISM: Gossypium sp.
<220> FEATURE:
<221> NAME/KEY: variation
<222> LOCATION: (69)..(69)
<223> OTHER INFORMATION: SNP: marker DCTE1_365870_69

<400> SEQUENCE: 9
```

```
aaattaggcc acttgcagag cttaatgtga tgagcatctt ctgtcccttt acaagtaaac      60
aaagctcgrt gcttcttaaa caagataacc tttgaaagtt gaataattgg aacccaatgt     120
gactactgga ttccgggagt tccttggacc aaaagtggaa aaacctcagc agctgtacaa     180
agtccccagc ttgaagactg atagattag ataggtgtca tttataggct gtactgacac      240
cataaacaat attttgataa aacctaaacc aaaatatcct atacacaatg ccaaattata     300
cagaaatgaa agcaaatata gagctatact ttgttcatgg aaacaaatca ccttaattct     360
ttgttctttt tttc                                                      374
```

```
<210> SEQ ID NO 10
<211> LENGTH: 301
<212> TYPE: DNA
<213> ORGANISM: Gossypium sp.
<220> FEATURE:
<221> NAME/KEY: variation
<222> LOCATION: (151)..(151)
<223> OTHER INFORMATION: SNP: marker DASCTP_39375_356

<400> SEQUENCE: 10
```

```
aggatacctc taccactcaa tattcagaat gatagtcaat ggattggagt agcttcctgt      60
tgcatttttg tcaatgatga tgcttcccgg gataagttta tcaactgcag agctgttatc     120
cattgtagaa attctggaca aggcggtcga ratggatctg tcttccgaga tacagatctt     180
cgacgtgtcg atgcaagtag ttggttgttt gggaaacgtt ttaaccagcc cataacgaag     240
gatcacctat ttcttagata ttggtcgcgt gataaattat atccattttc cttagaggat     300
a                                                                    301
```

```
<210> SEQ ID NO 11
<211> LENGTH: 458
<212> TYPE: DNA
<213> ORGANISM: Gossypium sp.
<220> FEATURE:
<221> NAME/KEY: variation
<222> LOCATION: (347)..(347)
<223> OTHER INFORMATION: SNP: marker DCTE1_240643_347
```

<400> SEQUENCE: 11

```
attacctgat ctacacgcaa cacagtgcag gcagcatctg cagcatattt gagagcaaaa      60
aacctgacaa aaaaagtcaa caattgtaaa ttataaaaga atcagaggtt aattttcgat     120
gcaaaagaga acagaactga gccagaaata attgtaaata gcgacttact tagtgacata     180
aaggtcccaa acattcacgg ttgagacatc cttgcaaaca caatcctcag agtcatctcc     240
cctcaagtcg atgcccactt tagcattccc agatgcatgc ttttcataca agttagaaat     300
aatatccatt ggtttgagtc cagcattctc tgccagggtt ctcggtrcca attcaaaact     360
ttcagcaaac ttagcaatgg catactgatc caatctgcaa aatatcccgt agttaatatt     420
aatagcttct tctagtactc atctaatcta ctataaat                             458
```

<210> SEQ ID NO 12
<211> LENGTH: 990
<212> TYPE: DNA
<213> ORGANISM: Gossypium sp.
<220> FEATURE:
<221> NAME/KEY: variation
<222> LOCATION: (501)..(501)
<223> OTHER INFORMATION: SNP: marker DCTE1_208529_965

<400> SEQUENCE: 12

```
agcgttgcct gccttccaag gatccctaaa attaggcctt aactttctct ccacaagcat      60
ccttggtccg tagactggtg actcctctgg tctatcatct tccaccatca ccgccatatc     120
cgccatagag tgtttcgcat aagccctgga agcccccttg ttcttgttgg agttggaatc     180
ctcaattgta aaagtcgctg tatcaaatat ttcgaccatt aatcaaacaa taacagaaac     240
ttaactaaat aggagaaaaa atcaatttgt acgaagggc tagtgaagta gtttacacaa     300
ttattgcttc tttcctgatc ggcccgttat aaaattcaaa aagttttgaa tccttttagg     360
tgcggccctt cttcctctgt ttccacgtcg atatcacgtt ttcgttttac aagggaagtg     420
ctgcctgcgg atccatcgtt ttcagtagag tgatgatgga tatgttccaa gtttggagaa     480
gattgaatgg tatggcactg yagctcttyt atttcttcca aatctttctc atacattatt     540
ctaacaccac acttcttcac cttaacagaa ggatacctt ttggagaaga ttggaaagac      600
atctcaagcg ataaatcctt ggcttcacat ttatccttta atgataatgg cgagaaatat     660
cgaagaaaaa ggtggtcctt ctttatgcgt cgtccacaaa aattaaggaa actggaatcg     720
accattcgac tatttaact tgaaaaacag atccattact actagattgt ccagaatatc     780
tagaatggat ataagttgga ccaccgataa cctttatctc ggaaccatca tcatcaccga     840
aaatgcagca gaaagcaact ccaatacatt gactgtcatt ctgaatattg agaggcaaag     900
gtatttcgat tacagagccg cctctctgtt ggctgaacca ttctgggatt tcatttccag     960
gtataacagc atcaaatctt ttcttgaatt                                      990
```

<210> SEQ ID NO 13
<211> LENGTH: 357
<212> TYPE: DNA
<213> ORGANISM: Gossypium sp.
<220> FEATURE:
<221> NAME/KEY: variation
<222> LOCATION: (223)..(223)
<223> OTHER INFORMATION: SNP: marker DCTE1_271930_223

<400> SEQUENCE: 13

```
aattctcctc cattctattt gctcttcttt gctcttgtgc atagagaaca tttatcagct      60
ttgtcaaggg tatagctgat aggtccctag agtcctccaa agaagagatt tttgactcat     120
```

```
acttctctgg aagagttgta atgactttt caactatcct tttgtcactg aactaatcct    180
caagaagcct tatgttttt actgtagcca taatcctgtc agmatactag ttgatggttt    240
ctgactcttt catcttcaga ttctcgaagt cccttctcag gtttatcaac tgctactgcc    300
tggtcttatc tgacccttga actcttcctt gagtctgtcc caagcctact ttggagt      357
```

```
<210> SEQ ID NO 14
<211> LENGTH: 301
<212> TYPE: DNA
<213> ORGANISM: Gossypium sp.
<220> FEATURE:
<221> NAME/KEY: misc_feature
<222> LOCATION: (140)..(140)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_59246_191
<220> FEATURE:
<221> NAME/KEY: misc_feature
<222> LOCATION: (292)..(292)
<223> OTHER INFORMATION: n is a, t, c or g

<400> SEQUENCE: 14
```

```
aggggttgag ttaatgattt taccgcaaat gataaccgtg ttagttgatt ttacgagtgc     60
agaagacttc agctgtgaca tcgagtctga tggaaaagtg ctaatcaaag ggataacaac    120
aaccggtgag aaagttgtan gtcaagaact ytcaagtctt tcatatgctc acacaaaatt    180
tatgcccatc tggacacttc actgtttcat tcgagctacc gggccctgtc gatcccgaaa    240
aagttactag ttgtttagct aatggattgc ttgaagccgt tgtgaagaaa anggtaactg    300
a                                                                   301
```

```
<210> SEQ ID NO 15
<211> LENGTH: 301
<212> TYPE: DNA
<213> ORGANISM: Gossypium sp.
<220> FEATURE:
<221> NAME/KEY: misc_feature
<222> LOCATION: (57)..(57)
<223> OTHER INFORMATION: n is a, t, c or g
<220> FEATURE:
<221> NAME/KEY: misc_feature
<222> LOCATION: (73)..(73)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_28910_164

<400> SEQUENCE: 15
```

```
agcgttacct tcttgttttc ggtgggagtt cacatgctac tttcttcaat gatttgncat     60
gtccttgatt tgncaaactg taagataatt cactttca gttttctcat tgcttgtct       120 gaggaattaa tttctttatc tttccttctt ytttttttct ttctttttt tggtatttgg    180 atttgtagat ggaatggtca aaacctgcac aactaggtga gttaccaact cctagagctg    240
gtcatgcagg agtgactatt ggggaaaact ggtttattgc tggaggtgga gacaacaaaa    300
g                                                                   301
```

```
<210> SEQ ID NO 16
<211> LENGTH: 301
<212> TYPE: DNA
<213> ORGANISM: Gossypium sp.
<220> FEATURE:
```

<221> NAME/KEY: variation
<222> LOCATION: (151)..(151)
<223> OTHER INFORMATION: SNP: marker DASCTP_1656_527
<220> FEATURE:
<221> NAME/KEY: misc_feature
<222> LOCATION: (192)..(192)
<223> OTHER INFORMATION: n is a, t, c or g
<220> FEATURE:
<221> NAME/KEY: misc_feature
<222> LOCATION: (200)..(200)
<223> OTHER INFORMATION: n is a, t, c or g
<220> FEATURE:
<221> NAME/KEY: misc_feature
<222> LOCATION: (212)..(212)
<223> OTHER INFORMATION: n is a, t, c or g
<220> FEATURE:
<221> NAME/KEY: misc_feature
<222> LOCATION: (245)..(245)
<223> OTHER INFORMATION: n is a, t, c or g

<400> SEQUENCE: 16

```
gtgccggaat ggcacccgcc attcccgaaa cttctgcatg aaaatcgtaa aactatgaaa    60
aattacatta aaaaaggctt aaatatcaag aaagaagagc caaatatta cttaattcat   120
ttggaatttg tcccttcctc cccatttccg kacataattg ttctacggga actttcgctg   180
ctaatttagg tngatttagn agattttggg tncctaagga atgcaccgaa cttctagctt   240
ttgtngcatt ccttcacggc tgtcatccca gaacagtcta attctactga ttcgccacta   300
t                                                                   301
```

<210> SEQ ID NO 17
<211> LENGTH: 293
<212> TYPE: DNA
<213> ORGANISM: Gossypium sp.
<220> FEATURE:
<221> NAME/KEY: misc_feature
<222> LOCATION: (82)..(82)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_51689_504
<220> FEATURE:
<221> NAME/KEY: misc_feature
<222> LOCATION: (220)..(220)
<223> OTHER INFORMATION: n is a, t, c or g

<400> SEQUENCE: 17

```
aatatggaat caaagttcat acagattgct ttatatgcaa ggtattgtaa cacaaagtaa    60
aaacaggaag ggaaaacaaa anggagtcaa ttttggccat ctatctactc aataagctta   120
aaaaactcac ctagtcctgg aactgccaag rgtgagttct aggtcatccg atccgcaatc   180
ttcatgaatc ctctctcctt cccacggttt cacgagtccn tgttgcattg cttccaaatg   240
cgaactcgtc tgatataact tcagacattg gaacatcagc cgtatgatct gat           293
```

<210> SEQ ID NO 18
<211> LENGTH: 624
<212> TYPE: DNA
<213> ORGANISM: Gossypium sp.
<220> FEATURE:
<221> NAME/KEY: variation
<222> LOCATION: (124)..(124)
<223> OTHER INFORMATION: SNP: marker DCTE1_214869_124

<400> SEQUENCE: 18

```
tgtcatacat aagtcatgca cctaatgtac taacttttgg cttcgatatc aatggagcat    60
taactttcaa tacatcgaag cacatgagtt aggtactagg ggcgagtatt caatcgagtt   120
```
gagkcaaatc aagtaaaaaa aatttcgagt tgttgagtt gatgaatcct attttagcaa    180
ctgaactcaa tttaaatttt tcgaatcgaa tcgaatctag tcaaaaaatt tcgagtcaag    240
tcgagtcgag ttaacgaatc ctattattga tactcaatgt tgcgtttaca tggatcgatt    300
atttaactag tagacgaagt acgagattat ttaactacat aaacaataca attgttttgt    360
cttttaattt aatgggtcaa cgtttatcaa ataacgtag ttttgccttt caacttaatg    420
gttttgactt ttaactttta aaaagtaaa catttatcaa aacgacatag ttttggcttt    480
tcttattcgg attttcggat aactcgaatt gtgtaattca tattcaagtt aaaccgaaaa    540
acttaatttt ttattcgagt tgatctgaat aacttgatta actcaaataa ctcgaactat    600
ttaattcaaa attaaatttt ttat    624

```
<210> SEQ ID NO 19
<211> LENGTH: 301
<212> TYPE: DNA
<213> ORGANISM: Gossypium sp.
<220> FEATURE:
<221> NAME/KEY: misc_feature
<222> LOCATION: (23)..(23)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_8602_496
<220> FEATURE:
<221> NAME/KEY: misc_feature
<222> LOCATION: (267)..(267)
<223> OTHER INFORMATION: n is a, t, c or g

<400> SEQUENCE: 19
```
gcaacagatc aagtgaccta aanttggcgc ggcctaatct cctatgccaa agaccaatgc    60
tatcagcaag acgagtataa gccttttctct caatttgact cacatcaagc ataaaacacc    120
tattaatcat agttactata actagctcct raccaaatga gtcttaaaca atgcacgaac    180
catctctaaa gaccaaagtg tatcatttta cactaactga ctaacactaa gtaagttctg    240
gtctatgtca ggcacaaaaa gcacatncag aaattacttt gttacctgaa ctagagttga    300
t    301

```
<210> SEQ ID NO 20
<211> LENGTH: 301
<212> TYPE: DNA
<213> ORGANISM: Gossypium sp.
<220> FEATURE:
<221> NAME/KEY: misc_feature
<222> LOCATION: (101)..(101)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_8602_418

<400> SEQUENCE: 20
```
gcttaccaag ctgacaaact tcacaaacag tatcattgac ctcaaccttg gacatgtcct    60
caaccaagtt cagcctgtgc aacagatcaa gtgacctaaa nttggcgcgg cctaatctcc    120
tatgccaaag accaatgcta tcagcaagac kagtataagc ctttctctca atttgactca    180
catcaagcat aaaacaccta ttaatcatag ttactataac tagctcctaa ccaaatgagt    240
ctttaacaat gcacgaacca tctctaaaga ccaaagtgta tcattttaca ctaactgact    300
a    301

<210> SEQ ID NO 21
<211> LENGTH: 274
<212> TYPE: DNA
<213> ORGANISM: Gossypium sp.
<220> FEATURE:
<221> NAME/KEY: misc_feature
<222> LOCATION: (116)..(116)
<223> OTHER INFORMATION: n is a, t, c or g
<220> FEATURE:
<221> NAME/KEY: variation
<222> LOCATION: (151)..(151)
<223> OTHER INFORMATION: SNP: marker DASCTP_10515_556

<400> SEQUENCE: 21
gctgcttgga atttgtttgc tcaaaatgct ggtgatgtgg ttgaagtacc aagcattaat     60
ccactagcaa gggcagttgc aaaagaatgc ggcggtttgc cattagctct caaaancggt    120
tgggaagtca atgaggaaca aaagaaggat ygagttgtgg aaacacgcac ttcaccattt    180
gcagcattca gaccctcacg tcaaacacat cgaggacgaa gtctatcgtc gtttaaagtt    240
gagttacgac tcattgccaa gtaagatcct gcag                                274

<210> SEQ ID NO 22
<211> LENGTH: 20
<212> TYPE: DNA
<213> ORGANISM: Artificial
<220> FEATURE:
<223> OTHER INFORMATION: oligonucleotide primer

<400> SEQUENCE: 22
catgtccaat ggatgtgtca                                                 20

<210> SEQ ID NO 23
<211> LENGTH: 20
<212> TYPE: DNA
<213> ORGANISM: Artificial
<220> FEATURE:
<223> OTHER INFORMATION: oligonucleotide primer

<400> SEQUENCE: 23
gggccactta aaggcattct                                                 20

<210> SEQ ID NO 24
<211> LENGTH: 20
<212> TYPE: DNA
<213> ORGANISM: Artificial
<220> FEATURE:
<223> OTHER INFORMATION: oligonucleotide primer

<400> SEQUENCE: 24
acatttccac ccaagtccaa                                                 20

<210> SEQ ID NO 25
<211> LENGTH: 20
<212> TYPE: DNA
<213> ORGANISM: Artificial
<220> FEATURE:
<223> OTHER INFORMATION: oligonucleotide primer

<400> SEQUENCE: 25
aatcgttgac agcactgcac                                                 20

<210> SEQ ID NO 26
<211> LENGTH: 21
<212> TYPE: DNA
<213> ORGANISM: Artificial

```
<220> FEATURE:
<223> OTHER INFORMATION: oligonucleotide primer

<400> SEQUENCE: 26
tcatggaaca ccaaagttgg a                                              21

<210> SEQ ID NO 27
<211> LENGTH: 25
<212> TYPE: DNA
<213> ORGANISM: Artificial
<220> FEATURE:
<223> OTHER INFORMATION: oligonucleotide primer

<400> SEQUENCE: 27
acatgataga ttattcagca atgca                                          25
```